ns Patent [19]

United States Patent [19]

Fujii et al.

[11] Patent Number: 4,950,662

[45] Date of Patent: Aug. 21, 1990

[54] 2-OXA-ISOCEPHEM COMPOUNDS, COMPOSITIONS CONTAINING THE SAME AND PROCESSES FOR PREPARING THE SAME

[75] Inventors: Setsuro Fujii, Kyoto; Hiroshi Ishikawa; Koichi Yasumura, both of Otsu; Koichiro Jitsukawa, Ashiya; Sachio Toyama, Otsu; Hidetsugu Tsubouchi, Otsu; Kimio Sudo, Otsu; Koichi Tsuji, Otsu, all of Japan

[73] Assignee: Otsuka Pharmaceutical Co., Ltd., Tokyo, Japan

[21] Appl. No.: 261,293

[22] Filed: Oct. 24, 1988

[30] Foreign Application Priority Data

Oct. 22, 1987 [JP] Japan .................................. 62-267659
Oct. 22, 1987 [JP] Japan .................................. 62-267658

[51] Int. Cl.$^5$ .................... A61K 31/535; C07D 498/04
[52] U.S. Cl. ........................................ 514/210; 540/205
[58] Field of Search ........................ 540/205; 514/210

[56] References Cited

U.S. PATENT DOCUMENTS

| 4,013,648 | 3/1977 | Horning et al. | 260/244 |
|---|---|---|---|
| 4,386,089 | 5/1983 | Konig et al. | 424/246 |
| 4,476,124 | 10/1984 | Heymes et al. | 424/246 |
| 4,631,275 | 12/1986 | Hartwig et al. | 514/210 |
| 4,645,769 | 2/1987 | Shibahara et al. | 514/210 |

FOREIGN PATENT DOCUMENTS

| 0215435 | 3/1987 | European Pat. Off. . |
| 57-192387 | 11/1982 | Japan . |
| 2098217 | 11/1982 | United Kingdom . |
| 0193858 | 9/1986 | United Kingdom . |

Primary Examiner—Mukund J. Shah
Assistant Examiner—C. Cseh
Attorney, Agent, or Firm—Sughrue, Mion, Zinn, Macpeak & Seas

[57] ABSTRACT

There is described a 2-oxa-isocephem compound of the formula:

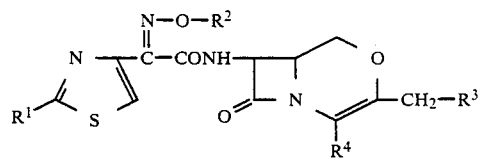

wherein $R^1$, $R^2$ and $R^4$ are as defined, and $R^3$ is a group of the formula:

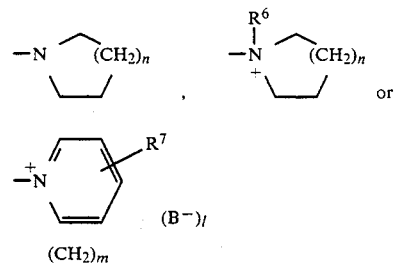

wherein n, m, $R^6$, $R^7$, $B^-$ and l are as defined, or pharmaceutically acceptable salt thereof. The compound has antimicrobial activity.

14 Claims, No Drawings

2-OXA-ISOCEPHEM COMPOUNDS, COMPOSITIONS CONTAINING THE SAME AND PROCESSES FOR PREPARING THE SAME

FIELD OF THE INVENTION

This invention relates to new 2-oxa-isocephem compounds and pharmaceutically acceptable salts thereof which are useful as antimicrobial compounds, processes for preparing the same, and pharmaceutical compositions containing the 2-oxa-isocephem compounds or salts thereof.

BACKGROUND OF INVENTION

Various 2-oxa-isocephem compounds are known which have antimiCrObial activity as described in Japanese unexamined patent publication No. 57-192587.

However, the 2-oxa-isocephem compounds of this invention are structurally different from the conventional 2-oxa-isocephem compounds,

SUMMARY OF THE INVENTION

One object of this invention is to provide 2-oxa-isocephem compounds having antimicrobial activity.

Another object of this invention is to provide a pharmaceutical composition containing the 2-oxaisocephem compounds in an antimicrobially effective amount.

A further object of this invention is to provide a process for preparing the 2-oxa-isocephem compounds and pharmaceuticallY acceptable salts thereof.

According to this invention, there is provided a 2-oxa-isocephem compound of the following formula (1), pharmaceutically acceptable salts thereof.

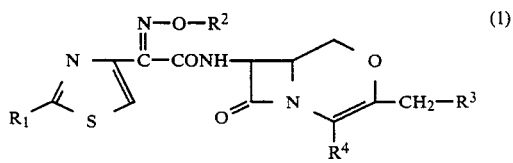

wherein $R^1$ is an amino group which may have a protective group; $R^2$ is $C_1$-$C_6$ alkyl group, $C_3$-$C_8$ cycloalkyl group which may be substituted with carboxyl group, cycloalkylalkyl group having $C_3$-$C_8$ cycloalkyl moiety and $C_1$-$C_6$ alkyl moiety, $C_2$-$C_6$ alkenyl group, $C_2$-$C_6$ alkynyl group or a group of the formula:

$$-A-R^5$$

wherein, A is a $C_1$-$C_6$ alkynyl group, $R^5$ is carboxy group or carbamoyl group;

$R^3$ is a group represented by the formula:

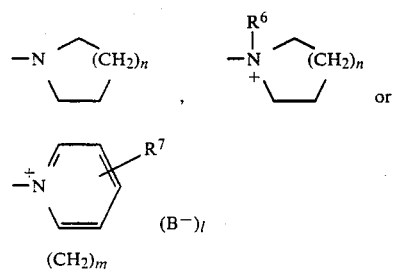

wherein n is I or 2, m is an integer from 0 to 4, $R^6$ is $C_1$-$C_6$ alkyl group, $C_2$-$C_6$ alkenyl group, or a group of the formula:

$$-D-R^8$$

wherein D is $C_{1-D6}$ alkylene group, $R^8$ is hydroxyl group, carbamoyl group, cycloalkyl group, or $C_1$-$C_6$ alkanoyl group;

$R^7$ is hydrogen atom, cyanoalkylthio group having $C_1$-$C_6$ alkyl moiety, carbamoyl group or unsaturated heteroclic 5-menbered ring group which has 1 to 3 hetero-atoms selected from the group consisting of nitrogen atom and oxygen atom; $B^-$ is anion; l is 0 or 1; the above mentioned groups of the formulas:

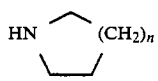

and

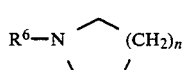

may form a condensed ring with a benzene ring which may have 1 or 2 substituent groups selected from the group consisting of hydroxyl group , $C_1$-$C_6$ alkoxyl group or $C_1$-$C_6$ alkanoyloxy group; and $R^4$ is carboxylate group, carboxyl group or, esterificated carboxyl group.

When $R^4$ is carboxylate group, l represents 0, and when $R^4$ is carboxy group or esterified carboxy group, l represents 1.

Also, this invention provides an antimicrobial composition containing the compound of the formula (1) or pharmaceutically acceptable salts in an antimicrobially effective amount.

Furthermore, this invention provides a process for preparing the compounds of formula (1) and pharmaceutically acceptable salts thereof.

The compound of general formula (1) according to the present invention has high antimicrobial activity against a broad spectrum of gram-positive and gram-negative bacteria, displaying particularly high activity against gram-positive bacteria such as *Staphyloccocus aureus* (FDA-209-P), *Streptococcus pneumoiae* and *Corynebacterium diphteria*.

The compound according to the present invention is further characterized by good absorption, long duration of effect, low toxicity and excellent effects on resisitant strains and clinically isolated strains of bacteria. Moreover, the compound is highly stable and has a satisfactory pharemacokinetic profile. Thus, the compound shows a high renal excretion and a good transfer into the bile. It is well distributed in various organs including the lungs. The difference between minimal inhibitory concentration and minimal bactericidal concentration is small. Furthermore, the compound has few side effects such as immunosuppression and allergy.

Therefore, the compound according to the present invention is also useful as a therapeutic agent for the diseases caused by various pathogenic bacteria in man, animals and fish or as an external microbicide or disinfectant for medical devices, instruments end so on.

DETAILED DESCRIPTION OF THE INVENTION

The group given in terms of symbols in the above general formula (1) are respectively described in more detail in the following.

Examples of the protecting group of amino group are $C_1$–$C_6$ alkanoyl group, such as formyl, acetyl, propyonyl, butyryl, iso-butyryl, pentanoyl, hexanoyl; $C_2$–$C_6$ alkanoyl group, which is substituted with 1 to 3 harogen atoms, such as monochloroacetyl, monofluoroacetyl, monobromoacetyl, monoiodoacetyl, dichloroacetyl, trichloroacetyl, trifluoroactyl, 3-chloropropionyl, 2,3-dichloropropionyl, 3,3,3-trichloropropionyl, 4-chlorobutyryl, 5-chloropentanoyl, 6-chlorohexanoyl, 3-fluoropropionyl, 4-fluorobutyryl; phenylalkyl group having 1 to 3 phenyl groups and $C_1$–$C_6$ alkyl moiety, such as, benzyl, -phenethyl, -phenethyl, 3-phenylpropyl, benzhydryl, trityl; phenylalkoxycarbonyl group having $C_1$–$C_6$ alkoxy group, such as phenylalkoxycarbonyl, 1-phenylethoxycarbonyl, 2-phenylethoxycarbonyl,3-phenylpropoxycarboxy, 4-phenylbutoxycarbonyl, 5-phenylpentyloxycarbonyl, 6-phenylhexyloxycarbonyl; alkoxycarbonyl group having $C_1$–$C_6$ alkoxy moiety, such as, metoxycarbonyl, ethoxycarbonyl, propoxycarbonyl, isopropoxycarbonyl, butoxycarbonyl, tertiary butoxycarbonyl, pentyloxycarbonyl, hexyloxycarbonyl.

Examples of the $C_1$–$C_6$ elkynyl group include methyl, ethyl, propyl, isopropyl, butyl, isobutyl, tertiary-butyl, pentyl, hexyl, or the like.

Examples of the cycloalkyl group which may be substituted with carboxyl group include cyclopropyl, cyclobutyl, cyclopentyl, cyclohexyl, cycloheptyl, cyclooctyl, carboxycyclopropyl, 1-carboxycyclobutyl, 1-carboxycyclopentyl, 2-carboxycyclopentyl, 3-carboxycyclopentyl, 1-carboxycycloheptyl, or the like.

Examples of the cycloalkylalkyl group having 1 to 6 carbon atoms in alkyl moiety and 3 to 8 carbon atoms in cycloalkyl moiety include cyclohexylmethyl, 2-cyclohexylethyl, 3-cyclohexylpropyl, 4-cyclohexylbutyl, 5-cyclohexylpentyl, 6-cyclohexylhexyl, cyclopropylmethyl, cyclopentylmethyl, 2-cycloheptylmethyl, cycloheptylmethyl, or the like.

Examples of the $C_2$–$C_6$ alkenyl group include vinyl, allyl, 2-butenyl, 3-butenyl, 1-methylallyl, 2-pentenyl, 2-hexenyl, or the like.

Examples of the $C_2$–$C_6$ alkynyl group include ethynyl, 1-propynyl, 2-propynyl, 2-butynyl, 1-methyl-2-propinyl, 2-pentynyl, 2-hexynyl, or the like.

Examples of the $C_1$–$C_6$ alkylene group include methylene, methylmethylene, dimethylmethylene, trimethylene, 1-methyltrimethylene, 2-methyltrimethylene, 2,2-dimethyltrimethylene, tetramethylene, pentamethylene, hexamethylene, or the like.

Examples of the heterocyclic moiety in heterocyclic group represented by the following formula:

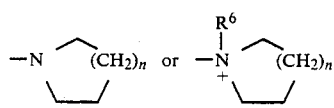

include those that can form a COndensed ring with a benzene ring may have 1 or 2 substituent groups selected from the group consisting of hydroxy group, $C_1$–$C_6$ alkoxy group and $C_1$–$C_6$ alkanoyloxy group, such as, 1-pyrrolidinyl, piperidino, 1-indolinyl, 2-isoindolinyl, 1,2,3,4-tetrahydroquinol-1-yl, 1,2,3,4-tetrahydroisoquinol-2-yl, 4-hydroxyindolin-1-yl, 5-hydroxyindolin-1-yl, 6-hydroxyindolin-1-yl, 7-hydroxyindolin-1-yl, 5 6-dihydroxyindolin-1-yl, 4,5-dihydroxyindolin-1-yl, 4-methoxyindolin-I-yl, 5-ethoxyindolin-1-yl, 6-puropoxyindolin-1-yl, 7-hexyloxyindolin-1-yl, 6,7-dimethoxyindolin-I-yl, 5,6-yindolin-1-yl, 4-acetoxyindolin1-yl, 5-propionyloxyindolin-1-yl, 6-hexanoyloxyindolin1yl, 4,5-diacetoxyindolin-1-yl, 5,6-diacetoxyindolin-1-yl, 5-hydroxy-1,2,3,4-tetrahydorquinol-1-yl, 6-hydroxy-1,2,3,4-tetrahydroquinol-1-yl, 7-hydroxy-1,2,3,4-tetrahydorquinol-1-yl, 8-hydroxy-I,2,3,4-tetrahydroquinol-1-yl, 5,6-dihydroxy-1,2,3,4-tetrahydroquinol-1-yl, 5,8-dihydroxy-1,2,3,4-tetrahydroquinol-1-yl, 5-methoxy-1,2,3,4-tetrahydroquinol-1-yl, 6-propoxy-1,2,3,4-tetrahydroquinol-I-yl, 7-hexyloxy-1,2,3,4-tetrahydroxyquinol-1-yl, 8-ethoxy-1,2,3,4-tetrahydroquinol-1-yl, 5,8-dimethoxy-1,2,3,4-tetrahydroquinol-1-yl, 6,7-dimethoxy-1,2,3,4-tetrahydroquinol-1-yl, 7,8-dimethoxy-1,2,3,4-tetrahydroquinol-1-yl, 5-acetoxy-1,2,3,4-tetrahydroquinol-1-yl, 6-hexanoyloxy-1,2,3,4-tetrahydroquinol-1yl, 7-butyryloxy-1,2,3,4-tetrahydroquinol-1-yl, 8-acetoxy-1,2,3,4-tetrahydroquinol-1-yl, 5,6-diacetoxy-1,2,3,4-tetrahydroquinol-1-yl, 6,7-diacetoxy-1,2,3,4-tetrahydroquinol-1-yl, 6,8-diacetoxy-1,2,3,4-tetrahydroquinol-1-yl, 4-hydroxyisoindolin-2-yl, 5-hydroxyisoindolin-2-yl, 4,5-dihydroxyisoindolin-2-yl, 4,6-dihydroxyisoindolin-2-yl, 4-methoxyisoindolin-2-yl, 5-butoxyisoindolin-2-yl, 5,6-diethoxyisoindolin-2-yl, 4-hexynoyloxyindolin-2-yl, 5-acetoxyisoindolin-2-yl, 5,6-diacetoxyisoindolin-2-yl, 4,6-diacetOxyisoindolin-2-yl, 5-hydroxy-1,2,3,4-tetraisohydroquinol-2-yl, 6-hydroxy-1,2,3,4-tetraisohydroquinol-2-yl, 7-hydroxy-1,2,3,4-tetraisohydroquinol-2-yl, 8-hydroxy-1,2,3,4-tetraisohydroquinol-2-yl, 5,8-dihydroxy-1,2,3,4-tetrahydroisoquinol-2-yl, 5,6-dihydroxy-1,2,3,4-tetrahydroisoquinol-2-yl, 5-methoxy-1,2,3,4-tetrahydroisoquinol-2-yl, 6-pentyloxy-1,2,3,4-tetrahydrotoisoquinol-2-yl, 7-ethoxy-1,2,3,4-tetrahydrotoisoquinol-2-yl, 7,8-dimethoxy-1,2,3,4-tetrahydroisoquinol-2-yl, 5,6-dimethoxy-1,2,3,4-tetrahydroisoquinol-2-yl, 5-acetoxy-1,2,3,4-tetrahydroisoquinol-2-yl, 5-methoxy-1,2,3,4-tetrahydroroisoquinol-2-yl, 6-pentyloxy-1,2,3,4-trahydroroisoquinol-2-yl, 7-ethoxy-1,2,3,4-tetrahydroroisoquinol-2-yl, 7,8-dimethoxy-1,2,3,4-tetrahydroroisoquinol-2-yl, 5,6-dimethoxy-1,2,3,4-tetrahydroroisoquinol-2-yl, 5-acetoxy-1,2,3,4-tetrahydroquinol-2-yl, 6-butylkoxy-1,2,3,4-tetrahydroquinol-2-yl, 7-hexyanoyloxy-1,2,3,4-tetrahydroquinol-2-yl, 8-acetoxy-1,2,3,4-tetrahydroquinol-2-yl, 5,6-diacetoxy-1,2,3,4-tetrahydroquinol-2-yl, 6,7-diacetoxy-1,2,3,4-tetrahydroquinol-2-yl, 7,8-diacetoxy-1,2,3,4-tetrahydroquinol-2-yl.

Examples of the $C_1$–$C_6$ alkoxy group include methoxy, ethoxy, isopropoxy, butoxy, tertiery-butoxy, hexyloxy, or the like.

Examples of the $C_1$–$C_6$ alkanoyloxy group include formyloxy, acetoxy, puropioxy, butilyloxy, isobutylyloxy, pentanoyloxy, hexynoyloxy or the like.

Examples of the cyano $C_1$–$C_6$ alkylthio group include cyanomethylthio, 1-cyanoethyltbio, 2-cyanopropylthio, 2-cyano-I-methylethylthio, 4-cyanobutylthio, 5-cyanopentylthio,6-cyanohexylthio or the like.

Examples of the unsaturated 5-menbered heterocyclic ring group having 1 to 3 hetero atoms selected from the group consisting of nitrogen atom and oxygen atom, include furyl group, pyrrolyl group, 2H-pyrrolyl group, imidazolyl group, pyrazolyl group, 1H-2-oxazoyl, 4-oxazoyl, 5-oxazoyl, 1,2,3-triazolyl group, isoxazoyl group, oxazoyl group, 1,2,4-oxadiazolyl, 1,2,5-oxadiazolyl, 1,2,3-oxadiazolyl group, such as 2-furyl, 3-furyl, 1-pyrrolyl 2-pyrrolyl, 3-pyrrolyl, 2H-pyrrolyl-2-yl, 2H-pyrrol-3-yl, 2H-pyrrol-4-yl, 2H-pyrrol-5-yl, 1-imidazolyl, 2-imidazolyl, 4-imidazolyl, 5-imidazolyl, 1-pyrazolyl, 3-pyrazolyl, 4-pyrazolyl, 5-pyrazolyl, 1H-3-triazol-1-yl 1H-1,2,4-triazol-3-yl, 1H-1,2,4-triazol-5-yl, 1H-1,2,3-triazol-1yl, 1H-1,2,3-triazol-4-yl, 1H-1,2,3-triazol-5yl, 3-isoxazolyl, 4-isoxazolyl, 5-isoxazolyl, 2-oxazolyl, 4-oxazolyl, 5-oxazolyl, 1,2,4-oxadiazol-3-yl, 1,2,4-oxadiazol-5-yl, 1,2,5-oxadiazol-3-yl, 1,2,3-oxadiazol-4-yl, 1,2,3-oxydiazolyl-5-yl, Examples of the ester residue in the esterified carboxyl group include the conventional ester residues, for example, $C_1-C_6$ alkyl group, such as methyl, ethyl, propyl, isopropyl, butyl, isobutyl, tertiary-butyl, pentyl, hexyl, or the like: (mono- or di-)phenyl $C_1-C_6$ alkyl group, such as, benzyl, benzhydryl, α-phenethyl, β-phenethyl, α,β-diphenylethyl, 3-phenylpropyl, 4-phenylbutyl, 5-phenylpentyl, 6-phenylhexyl, or the like: $C_2-C_6$ alkenyl group, such as vinyl, allyl, crotyl, 2-pentenyl, 2-hexenyl, or the like; $C_3-C_8$ cycloalkyl group, such as cyclopropyl, cyclobutyl, cyclopentyl, cyclohexyl, cycloheptyl, cyclooctyl, or the like; and cycloalkyl alkyl groups containing 3 to 8 carbon atoms in the cycloalkyl moiety and 1 to 6 carbon atoms in the alkyl moiety, such as cYclohexylmethyl, 2-cyclohexylethyl, 3-cyclohexylpropyl, 4-cyclohexylbutyl, 5-cyclohexylpentyl, 6-cyclohexylhexyl, cyclopropylmethyl, 2-cyclobutylethyl, cyclopentylmethyl, 2-cycloheptylethyl, cyclooctylmethyl or the like.

The phenyl moiety in the (mono- or di-)phenyl alkyl group of the ester residue may optionally have 1 to 3 substituent groups selected from the group consisting of halogen atom, such as chlorine, bromine, fluorine and iodine atoms; $C_1-C_6$ alkyl groups, such as, methyl, ethyl, propyl, isopropyl, butyl, isobutyl, tertiary-butyl, pentyl, hexyl, or the like; $C_1-C_6$ alkoxy group, such as methoxy, ethoxy, propoxy, isopropoxy, butoxy, tertiarY-butoxy, pentyloxy, hexyloxy, or the like; nitro group; cYano group; alkoxyoarbonyl groups containing $C_1-C_6$ alkoxy moiety, such as methoxycarbonyl, ethoxycarbonyl propoxycarbonyl isopropoxycarbonyl, butoxycarbonyl, tertiary-butoxycarbonyl, pentyloxycarbonyl, hexyloxycarbonyl, or the like; and alkanoyloxy groups containing $C_1-C_6$ alkanoyl moiety, such as acetyloxy, propionyloxy, butyryloxy, isobutyryloxy, pentanoyloxy, hexanoyloxy, or the like; or a $C_1-C_6$ alkylenedioxy group, such as, methylenedioxy, ethylenedioxy, trimethylenedioxy, tetramethylenedioxy, or the like.

Further, the $C_1-C_6$ alkyl group employed as ester residue may optionally have 1 to 3 halogen atoms, alkoxy group, alkanoyloxy group, nitro group; cyano group; amino group; alkanoylamino group, or $C_1-C_6$ alkylthio group, such as, methylthio, ethylthio, propionylthio, butylthio or the like.

When $R^3$ is the group represented in the formula given below,

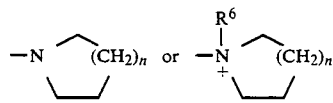

representative examples of the compound of the present invention which has the general formula (1) given below are shown in the following table.

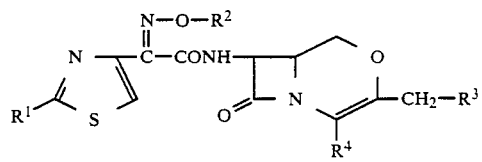

| | $R^1$ | $R^2$ | $R^3$ | $R^4$ | Remarks |
|---|---|---|---|---|---|
| 1 | $-NHC(C_6H_5)_3$ | $-CH_3$ | -N⟨pyrrolidine⟩ | $-\overset{O}{\overset{\|}{C}}OCH(C_6H_5)_2$ | |
| 2 | $-NH_2$ | $-CH_3$ | -N⟨pyrrolidine⟩ | $-COOH$ | |
| 3 | $-NHC(C_6H_5)_3$ | $-CH_3$ | $-\overset{+}{N}(CH_3)$⟨pyrrolidine⟩ | $-\overset{O}{\overset{\|}{C}}OCH(C_6H_5)_2$ | methanesulfonate |
| 4 | $-NH_2$ | $-CH_3$ | $-\overset{+}{N}(CH_3)$⟨pyrrolidine⟩ | $-COO^-$ | |

-continued

Structure:
$$\text{R}^1\text{-thiazole-C(=N-O-R}^2\text{)-CONH-[β-lactam with CH}_2\text{-O-C(R}^4\text{)=C-CH}_2\text{-R}^3\text{]}$$

| | $R^1$ | $R^2$ | $R^3$ | $R^4$ | Remarks |
|---|---|---|---|---|---|
| 5 | $-NHC(C_6H_5)_3$ | $-CH_3$ | -N-tetrahydroisoquinolinyl | $-\overset{O}{\underset{\|}{C}}OCH(C_6H_5)_2$ | |
| 6 | $-NH_2$ | $-CH_3$ | -N-tetrahydroisoquinolinyl | $-\overset{O}{\underset{\|}{C}}OCH(C_6H_5)_2$ | |
| 7 | $-NH_2$ | $-CH_3$ | -N-tetrahydroisoquinolinyl | $-COOH$ | |
| 8 | $-NHC(C_6H_5)_3$ | $-CH_3$ | -N$^+$(CH$_3$)-tetrahydroisoquinolinyl | $-\overset{O}{\underset{\|}{C}}OCH(C_6H_5)_2$ | iodide |
| 9 | $-NH_2$ | $-CH_3$ | -N$^+$(CH$_3$)-tetrahydroisoquinolinyl | $-COO^-$ | |
| 10 | $-NH_2$ | $-CH_3$ | -N$^+$(CH$_2$CONH$_2$)-pyrrolidinyl | $-COO^-$ | |
| 11 | $-NH_2$ | $-CH_3$ | -N$^+$(CH$_2$COCH$_3$)-pyrrolidinyl | $-COO^-$ | |
| 12 | $-NH_2$ | $-CH_3$ | -N$^+$(CH$_2$CH$_2$OH)-pyrrolidinyl | $-COO^-$ | |
| 13 | $-NH_2$ | cyclopropyl | -N$^+$(CH$_3$)-pyrrolidinyl | $-COO^-$ | |
| 14 | $-NH_2$ | cyclopentyl | -N$^+$(CH$_3$)-pyrrolidinyl | $-COO^-$ | |
| 15 | $-NH_2$ | $-CH_2-$cyclopropyl | -N$^+$(CH$_3$)-pyrrolidinyl | $-COO^-$ | |

-continued
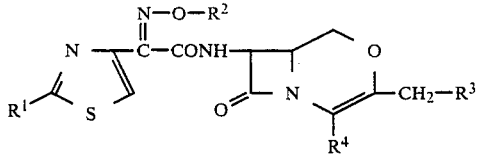
| | R¹ | R² | R³ | R⁴ | Remarks |
|---|---|---|---|---|---|
| 16 | —NH₂ | —CH₂CH=CH₂ |  | —COO⁻ | |
| 17 | —NH₂ | —CH₂C≡CH |  | —COO⁻ | |
| 18 | —NH₂ | —CH₂CH₃ |  | —COO⁻ | |
| 19 | —NH₂ | —CH₂CN |  | —COO⁻ | |
| 20 | —NH₂ | —CH₂CONH₂ |  | —COO⁻ | |
| 21 | —NH₂ | —CH₂COOH |  | —COO⁻ | |
| 22 | —NH₂ | 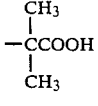 |  | —COO⁻ | |
| 23 | —NH₂ |  |  | —COO⁻ | |
| 24 | —NH₂ | —CH₃ |  | —COO⁻ | |
| 25 | —NH₂ | —CH₃ | 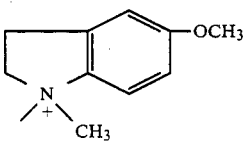 | —COO⁻ | |
| 26 | —NH₂ | —CH₃ | 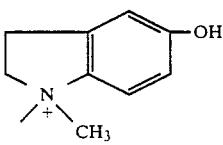 | —COO⁻ | |

-continued
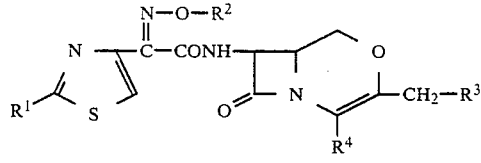
| | R¹ | R² | R³ | R⁴ | Remarks |
|---|---|---|---|---|---|
| 27 | $-NH_2$ | $-CH_3$ | 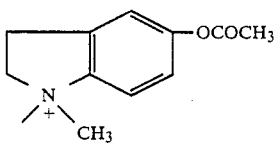 | $-COO^-$ | |
| 28 | $-NH_2$ | $-CH_3$ | 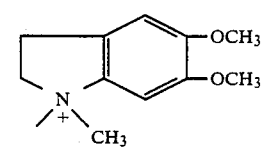 | $-COO^-$ | |
| 29 | $-NH_2$ | $-CH_3$ | 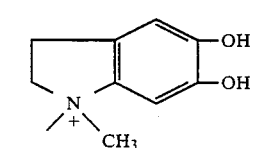 | $-COO^-$ | |
| 30 | $-NH_2$ | $-CH_3$ | 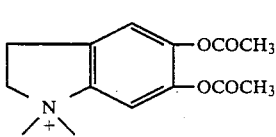 | $-COO^-$ | |
| 31 | $-NH_2$ | $-CH_2COOH$ | 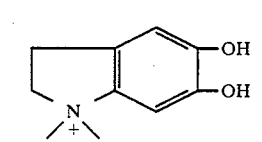 | $-COO^-$ | |
| 32 | $-NH_2$ | $-CH_2CN$ | 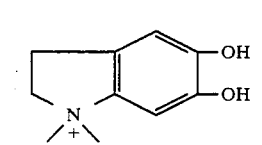 | $-COO^-$ | |
| 33 | $-NH_2$ | 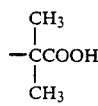 | 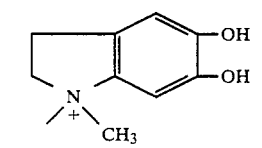 | $-COO^-$ | |
| 34 | $-NH_2$ | 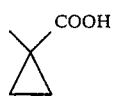 | 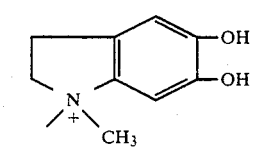 | $-COO^-$ | |
| 35 | $-NH_2$ | $-CH_2CH_3$ | 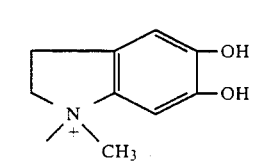 | $-COO^-$ | |

-continued

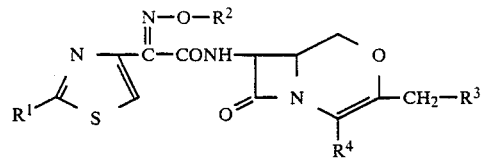

| | R¹ | R² | R³ | R⁴ | Remarks |
|---|---|---|---|---|---|
| 36 | $-NH_2$ | cyclopentyl | N-methyl-indolinium-5,6-diol | $-COO^-$ | |
| 37 | $-NH_2$ | $-CH_3$ | N-methyl-1,2,3,4-tetrahydroquinolinium-6,7-diol | $-COO^-$ | |
| 38 | $-NH_2$ | cyclopentyl | N-methyl-1,2,3,4-tetrahydroquinolinium-6,7-diol | $-COO^-$ | |
| 39 | $-NH_2$ | $-CH_3$ | N-allyl-indolinium-5,6-diol | $-COO^-$ | |
| 40 | $-NH_2$ | $-CH_3$ | N-(cyclopropylmethyl)-indolinium-5,6-diol | $-COO^-$ | |

In the compounds of the present invention, the representative examples of the compound represented by the following formula are shown in the following table.

And number of column for $R^7$ in the table shows the substituted position of $R^7$.

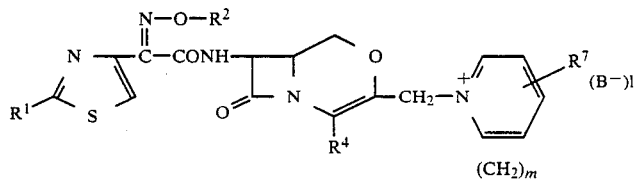

| | R¹ | R² | R³ | R⁴ | n | l | B⁻ |
|---|---|---|---|---|---|---|---|
| 1 | $-NHC(C_6H_5)_3$ | $-CH_3$ | H | $-COCH(C_6H_5)_2$ | 0 | 1 | methane-sulfonate |
| 2 | $-NH_2$ | $-CH_3$ | 4-$SCH_2CN$ | $-COO^-$ | 0 | 0 | — |
| 3 | $-NH_2$ | $-CH_3$ | 4-(1H-pyrazol-3-yl) | $-COO^-$ | 0 | 0 | — |

-continued
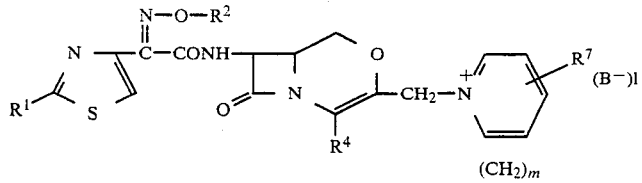
| | R¹ | R² | R³ | R⁴ | n | l | B⁻ |
|---|---|---|---|---|---|---|---|
| 4 | —NH₂ | —CH₃ | 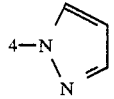 | —COO⁻ | 0 | 0 | — |
| 5 | —NH₂ | —CH₃ | 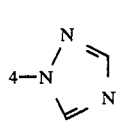 | —COO⁻ | 0 | 0 | — |
| 6 | —NH₂ | —CH₃ | 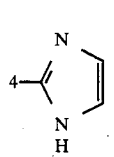 | —COO⁻ | 0 | 0 | — |
| 7 | —NH₂ | —CH₃ | 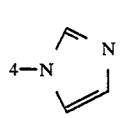 | —COO⁻ | 0 | 0 | — |
| 8 | —NH₂ | —CH₃ | 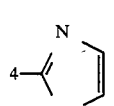 | —COO⁻ | 0 | 0 | — |
| 9 | —NH₂ | —CH₃ | 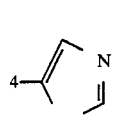 | —COO⁻ | 0 | 0 | — |
| 10 | —NH₂ | —CH₃ | 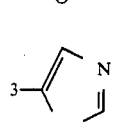 | —COO⁻ | 0 | 0 | — |
| 11 | —NH₂ | —CH₃ | 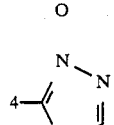 | —COO⁻ | 0 | 0 | — |
| 12 | —NH₂ | —CH₂CH₃ | 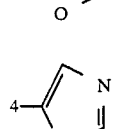 | —COO⁻ | 0 | 0 | — |
| 13 | —NH₂ | 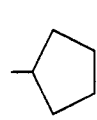 | 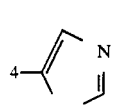 | —COO⁻ | 0 | 0 | — |
| 14 | —NH₂ | 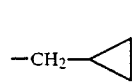 | 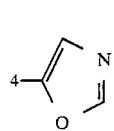 | —COO⁻ | 0 | 0 | — |

-continued

[Structure: thiazole-N-O-R² oxime with CONH linked to β-lactam bearing R⁴, CH₂-N⁺-pyridinium with R⁷, (CH₂)ₘ, (B⁻)l; R¹ on thiazole; R³ substituent]

| | R¹ | R² | R³ | R⁴ | n | l | B⁻ |
|---|---|---|---|---|---|---|---|
| 15 | —NH₂ | cyclopropyl | 4-oxazolyl | —COO⁻ | 0 | 0 | — |
| 16 | —NH₂ | —CH₂CH=CH₂ | 4-oxazolyl | —COO⁻ | 0 | 0 | — |
| 17 | —NH₂ | cyclohexyl | 4-oxazolyl | —COO⁻ | 0 | 0 | — |
| 18 | —NH₂ | —CHCN | 4-oxazolyl | —COO⁻ | 0 | 0 | — |
| 19 | —NH₂ | —CH₂COOH | 4-oxazolyl | —COO⁻ | 0 | 0 | — |
| 20 | —NH₂ | —C(CH₃)₂—COOH | 4-oxazolyl | —COO⁻ | 0 | 0 | — |
| 21 | —NH₂ | —CH₂C(O)NH₂ | 4-oxazolyl | —COO⁻ | 0 | 0 | — |
| 22 | —NH₂ | —CH₂C≡CH | 4-oxazolyl | —COO⁻ | 0 | 0 | — |
| 23 | —NH₂ | 1-(COOH)cyclopropyl | 4-oxazolyl | —COO⁻ | 0 | 0 | — |
| 24 | —NH₂ | —CH₃ | 4-CONH₂ | —COO⁻ | 0 | 0 | — |
| 25 | —NH₂ | cyclopentyl | 4-CONH₂ | —COO⁻ | 0 | 0 | — |
| 26 | —NH₂ | —CH₃ | H | —COO⁻ | 3 | 0 | — |
| 27 | —NH₂ | —CH₂CH₃ | H | —COO⁻ | 3 | 0 | — |
| 28 | —NH₂ | cyclopropyl | H | —COO⁻ | 3 | 0 | — |

-continued

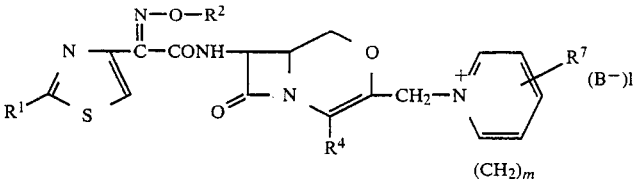

| | R¹ | R² | R³ | R⁴ | n | l | B⁻ |
|---|---|---|---|---|---|---|---|
| 29 | $-NH_2$ | $-CH_2-\triangleleft$ | H | $-COO^-$ | 3 | 0 | — |
| 30 | $-NH_2$ | $-CH_2CH=CH_2$ | H | $-COO^-$ | 3 | 0 | — |
| 31 | $-NH_2$ | $-CH_2C\equiv CH$ | H | $-COO^-$ | 3 | 0 | — |
| 32 | $-NH_2$ | cyclopentyl | H | $-COO^-$ | 3 | 0 | — |
| 33 | $-NH_2$ | $-CH_2CN$ | H | $-COO^-$ | 3 | 0 | — |
| 34 | $-NH_2$ | $-CH_2COOH$ | H | $-COO^-$ | 3 | 0 | — |
| 35 | $-NH_2$ | $-C(CH_3)_2-COOH$ | H | $-COO^-$ | 3 | 0 | — |
| 36 | $-NH_2$ | $-CH_3$ | H | $-COO^-$ | 4 | 0 | — |
| 37 | $-NH_3^+$ | $-CH_3$ | H | $-COOH$ | 0 | 1 | $SO_4^{2-}$ |

The compounds of the present invention can be produced by various processes, and the processes represented by the Reaction Scheme-1 to Reaction Scheme-5 can be mentioned by way of example.

substituted with halogen atom, arylsulfonyloxy group having or not having 1 to 3 substitutent groups selected from the group consisting of $C_1$-$C_6$ alkyl group, halogen atom, and nitro group; and $R^{4b}$ is carboxyl group or, Reaction Scheme-1

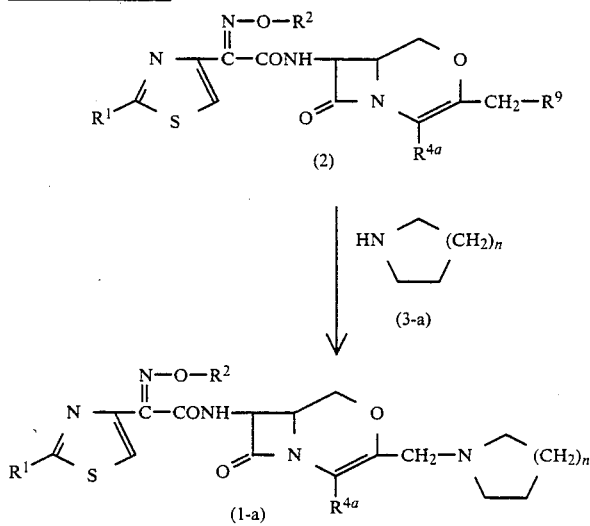

wherein $R^1$, $R^2$, n and the group of the formula:

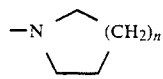

have the same meanings as defined above; $R^9$ is a halogen atom, $C_1$-$C_6$ alkanesulfonyloxy group that can be esterified carboxyl group.

The compound shown by following formula;

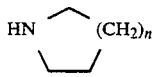

may form a condensed ring with the benzene ring having or not having I to 3 substitutent groups which are selected from the group consisting of hydroxyl group, $C_1$-$C_6$ alkoxyl group and $C_1$-$C_6$ alkanoyloxyl group.

The compound of the formula (1-a) which is one of the compound of the present invention, can be obtained by the reaction of the compound of the formula (2) with the compound of the formula (3-a) in presence of a suitable inert solvent.

Referring to $R^9$ in the compound of the formula (2), halogen atom means chloride atom, bromine atom, iodine atom or fluorine atom, and examples of $C_1$-$C_6$ alkanesulfonyloxy group which may have a halogen atom are methanesulfonyloxy, ethanesulfonyloxy, propanesulfonyloxy, trifluoromethanesulfonyloxy or the like. And, the examples of arylsulfonyloxy group which may be substituted with $C_1$-$C_6$ alkyl group, halogen atom or nitro group, is benzenesulfonyloxy, toluenesulfonyloxy, p-chlorobenzenesulfonyloxy, p-nitrobenzenesulfonyloxy or the like.

As the example of the solvent, there may be mentioned any solvent which does not adversely influence the reaction, ethers such as diethyl ether, tetrahydrofuran, dioxane or the like, halogenated hydrocarbons such as dichloromethane, dichloroethane, chloroform, carbon tetrachloride or the like, aromatic hydrocarbons such as benzene, toluene, xylene or the like, aliphatic hydrocarbons such as hexane, heptane or the like, alcohols such as methanol, ethanol, propanol or the like, aprotic polar solvents such as dimehylformamide (DMF), hexamethylphosphoric triamide (HMPA), dimethyl sulfoxide (DMSO) or the like, carbon disulfide and so on.

The compound of the formula (2) and the compound of the formula (3-a) are present in a molar ratio of 1:1 at least and preferably I:1 to 1:2. This reaction is conducted at $-10°$ C. to $100°$ C. and preferably at $0°$ C. to $50°$ C. Thus, the compound of the formula (1-a) can be obtained.

Referring to the obtained compound of the formula (1-a), when $R^1$ is a protected amino group, the compound of the formula (1-a) having amino group as $R^1$ can be produced by the elimination reaction of the aminoprotecting group from the compound of the formula (1-a). When $R^{4a}$ is an esterified carboxyl group, the compound of the compound (1-a) having a carboxyl group as R4a, can be produced by deesterification reaction. Further more, in the compound of the formula (1-a), when $R^1$ is the protected amino group and $R^{4a}$ is the esterified carboxyl group, the compound having a carboxyl group as $R^4$ and amino group as $R^1$ can be produced by elimination reaction of amino-protecting group and deesterification.

The elimination reaction of the amino-protecting group is carried out by the catalYtic reducing method or the method of using acid or base to the compound of the formula (1-a), in the absence of a solvent or in the presence of suitable inert solvent.

As examples of the inert solvent, there may be mentioned halogenated hydrocarbons such as dichloromethane, dichloroethane, chloroform, carbon tetrachloride or the like, acetates such as, ethylacetate, methylacetate or the like, ethers such as diethyl ether, tetrahydrofuran, dioxane or the like, aromatic hydrocarbons such as benzene, toluene, xylene or the like, amines such as pyridine, piperidine, triethylamine or the like, aliphatic hydrocarbons such as hexane, heptane or the like, alcohols such as methanol, ethanol, propanol or the like, aprotic polar solvents such as dimethylformamide (DMF), hexamethylphosphoric triamide (HMPA), dimethyl sulfoxide (DMSO) or the like, carbon disulfide, water and mixture solvent of water with the above mentioned solvent.

When water is added to the reaction system, its proportion relative to the acid or basic compound is preferably in the range of about 10 to 80 % by volume, and it is advantageous tO add a further amount of 10 to 20 volumes of water at completion of the reaction.

As examples of acid compound, there may be mentioned Lewis acid such as anhydrous alminium chloride, stannic chloride, tetra-titanium chloride. boron trichlorides, boron trifluoride-diethyl ether complex, zinic chloride; an inorganic acid such as hydrochloric acid, hydrobromic acid, sulfuric acid, nitric acid or the like; an organic acid such as trichloroacetic acid, &rifluoroacetic acid, methanesulfonic acid, acetic acid, formic acid or the like, an acid-type ion exchange resin and so on.

As examples of the base compound, there may be mentioned trialkylamines such as triethylamine, tributylamine or the like, other organic bases as pyridine, picoline, 1,5-diazabicycle [4,3,0]nonene-5, 1,4-diazabicycle[2,2,2]octane, 1,8-diazabicycle[5,4,0]undecene-7 or the like, inorganic bases such as alkali metal hydroxides, e.g. sodium hydroxide potassium hydroxide or the like, alkali metal carbonates, e.g. sodium carbonate, potassium carbonate or the like, alkali metal hydrogen carbonates, e.g. sodium hydrogen carbonate, potassium hydrogen carbonate or the like, and so on.

When the catalytic reduction method is used in the above reaction, as the examples of the catalyst used in the catalytic reducation may be mentioned platinum catalyst, e g, platinum oxide, platinum-black, platinum line, platinum plate, platinum sponge and colloidal platinum or the like, palladium catalyst e.g. palladium-black, palladium chloride, palladium oxide, palladium-carbon, palladium-barium sulfate, palladium sponge or the like, nickel catalyst e.g. reduced nickel, nickel oxide, Raney nickel or the like, cobalt catalyst e.g. reduced cobalt, Raney cobalt or the like, iron catalyst e.g. reduced iron, Raney iron or the like, copper catalyst e.g. reduced copper, Raney copper or the like, and so on.

When an acid or a base is used in &he above reaction, the acid or base and the compound of the formula (1-b) are present in a molar ratio of 1:1 to 100:1 and preferably 1:1 to 20:1. This reaction is conducted at $-20°$ C. to $80°$ C., preferably at $-10°$ C. to $50°$ C., and can be carried to completion in 30 minutes to 48 hours, preferably in 1 to 24 hours.

When the catalytic reduction method is employed, the catalytic reduction catalyst and the compound of the formula (1-b) are present in a molar ratio of 1:10 to 10:1 and preferably 0.1 to 1. This reaction is conducted at 0 to $200°$ C., preferably 0 to $100°$ C. and may be carried to completion in 30 minutes to 48 hours, preferably 30 minutes to about 6 hours.

The deesterification of the compound of the formula (1-a) is carried out in the presence of a hydrolysis catalyst without a solvent or in a suitable inert solution.

As inert solvent and hydrolysis catalyst, the include inert solvent and acid or base compound used in the elimination reaction of amino-protecting group can be employed.

The deesterification reaction can be carried out by the catalytic reduction method, when the ester residue of $R^{4a}$ is a such residue, e.g. a benzyl group, as can be easily cleaved. As catalysts used in the catalytic reduction method is the same catalysts as in elimination of amino-protecting group can be employed.

When an acid or a base is used in &he above reaction to the above reaction, the acid or base and the compound of the formula (1-a) are present in a molar ratio of 1:1 to 100:1 and preferably 1:1 to 20:1. This reaction is conducted at $-20°$ C. to $80°$ C., preferably at $-100°$ C. to $50°$ C., and can be carried to completion in 30 minutes to 48 hours, preferably in 1 to 24 hours.

When the catalytic reduction method is employed, the catalytic reduction catalyst and the compound of the formula (1-b) are present in a molar ratio of 10:1 to 1:10 and preferably 1:10 to 1:1. This reaction is conducted at 0 to $200°$ C., preferably 0 to $100°$ C. and may be carried to completion in 30 minutes to 48 hours, preferably 30 minutes to about 6 hours.

Also the compound of the formula:

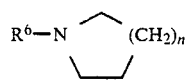

may form a condensed ring with the benzene ring which may have 1 to 3 substituent groups which are selected from the group consisting of hydroxy group, $C_1$-$C_6$ alkoxy group and $C_1$-$C_6$ alkanoyloxy group. And, when $R^{4b}$ is carboxyl group, l is 1, and when $R^{4b}$ is carboxylate group, l is 0.

Referring to the above Reaction Scheme, reaction of the compound of the formula (2) wi&h the compound of the formula (3-b) is carried out in the same condition as reaction of the compound of the formula (2) with the compound of the formula (3-a).

Referring to the compound of the formula (1-b), when $R^{4a}$is esterifed carboxyl group, the compound of the formula (1-c) can be obtained by deesterification of the compound of the formula (1-b). This deesterification can be carried out in the same condition as the deesterification described in the Reaction Scheme-1.

Reaction scheme-2

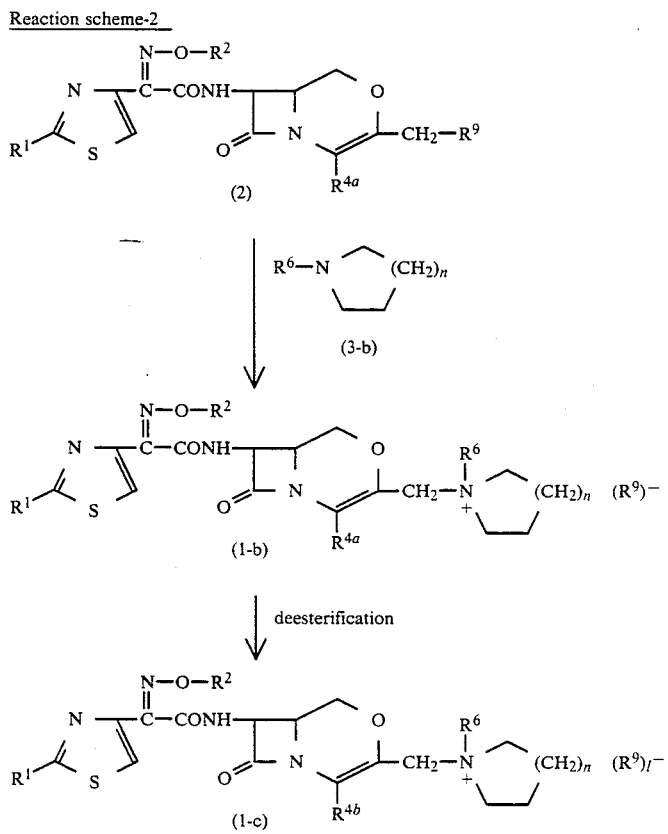

wherein $R^1$, $R^2$, $R^{4a}$, $R^6$, $R^9$, n and the group of the following formula:

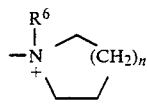

have the same meanings as defined above; and $R^{4b}$ is carboxyl group or carboxYlate group, and l is 0 or 1.

After the completion of the deesterification, the anion can be eliminated by purification by column chromatography using Diaion HP-20(Mitsubishi Chemical Industries), Amberlite XAD-2 (Rohm and Haas) or the like to give an inner salt.

On the other hand, after the completion of deesterification, when the anion is not eliminated, the compound that of the compound of the formula (1-c) is the carboxyl group is produced.

Referring to the compound of the formula (1-b) or the formula (1-c), when $R^1$ is protected amino group, the compound of which the corresponding $R^1$ is amino group can be produced in the same manner as the elimination reaction of an amino-protecting group shown in the Reaction Scheme 1.

to 50° C., and can be carried to completion in 30 minutes to 5 hours.

The examples of the anion supply agent used in this reaction are sulfuric acid, hydrochloric acid, methanesulfonic acid, trifluoroacetic acid, hydroblomo acid, hydroiodo acid, hydrofluoro acid or the like.

Reaction scheme-3

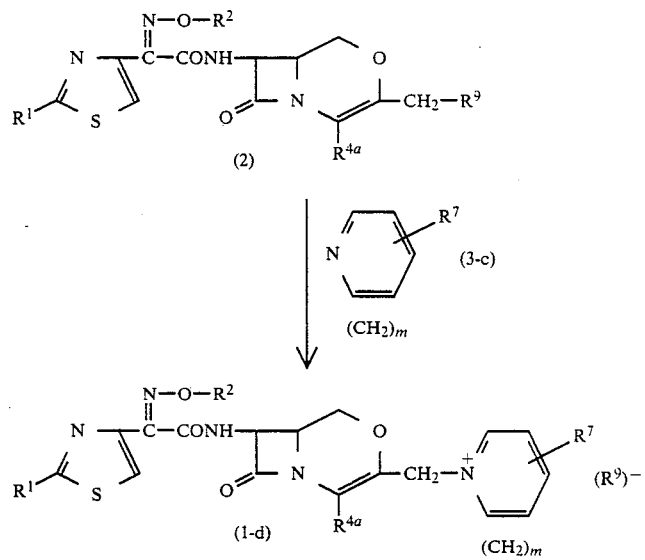

Referring to the compound of the formula (1-b) or the formula (1-c), the anion shown as $(R^9)^-$ can be changed another anion by anion exchange reaction.

The exchange reaction is carried out by the reacting the compound of the formula (1-c) or the formula (1-b) with an anion supply agent in the suitable inert solvent. The examples of the inert solvent are ethers such as diethyl ether, tetrahydrofuran, dioxane or the like, halogenated hydrocarbons such as dichloromethane, dichloroethane, chloroform, carbon tetrachloride or the like, aromatic hydrocarbons such as benzene, toluene, xYlene or the like. This reaction is conducted at $-10°$ C.

wherein $R^1$, $R^2$, $R^7$, $R^{4a}$, $R^9$ and m have the same meanings as defined above.

Referring to the above mentioned Reaction Scheme-3 the reaction of the compound of the formula (3-c) with the compound of the formula (2) is carried out in the same condition as reaction of the compound of the formula (2) with the compound of the formula (3-a), in the Reaction Scheme-1.

Referring to the compound of the formula (1-d) obtained, anion group shown as $(R^9)^-$ can be exchanged to another anion group in the same condition as the anion exchange reaction in the Reaction Scheme-2.

Reaction Scheme-4

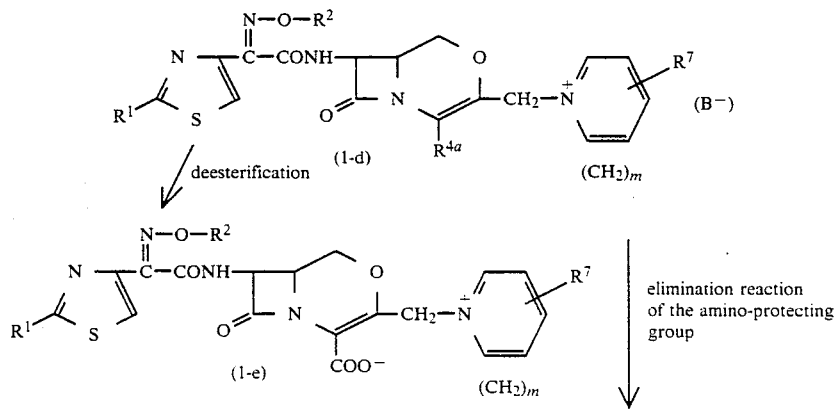

Reaction Scheme-4

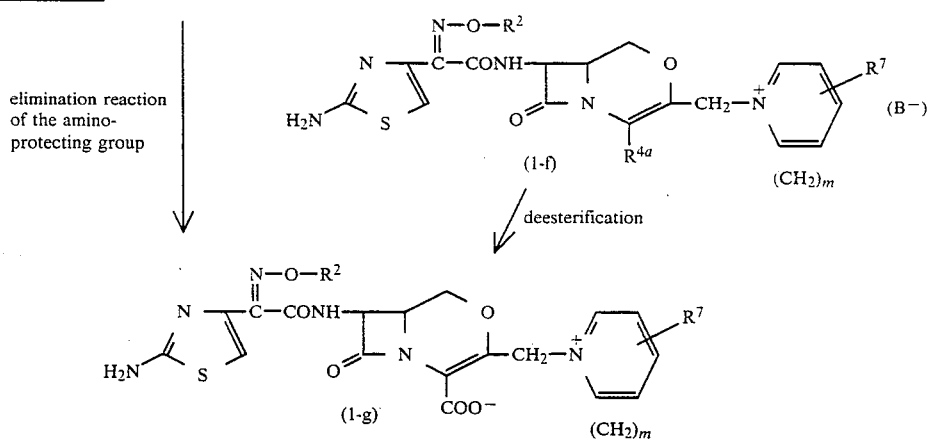

wherein $R^1$, $R^2$, $R^7$, $R^{4a}$, $B^-$ and m have the same meanings as defined above.

Referring the compound of the formula (1-d), when $R^4$ is the esterfied carboxyl group, the compound of the formula (1-e) according to the present invention, in which $R^4$ is carboxylate group, can be produced by deesterification reaction. When $R^1$ is the protected amino group, the compound of the formula (1-g), in which $R^1$ is amino group, can be produced by further elimination reaction of the amino-protecting group. Also, when $R^1$ is of the compound of the formula (1-d), is protected amino group, the compound of the formula (1-f) in which $R^1$ anion group, can be produced by elimination reaction of the amino-protecting group.

Furthermore, when $R^{4a}$ in the compound of the formula (1-f), is the esterified carboxyl group, the compound of the formula (!-g) having carboxylate group as $R^4$, can be produced by deesterification reaction.

In the above reaction, the deesterification reaction and elimination reaction of the amino-protecting group can be carried out of same time and in the same condition In this case, the compound of the present invention shown in the formula (1) in which $R^1$ and $R^4$ are respectively amino group carboxylate respectively group, is produced by one step.

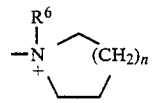

have the same meanings as defined above. However, when $R^4$ is carboxylate group, l is 0, and when $R^4$ is carboxyl group or esterified carboxyl group, l means 1.

The compound of the formula (1-h) is produced by the reaction between the compound of the formula (1-a) and the halide compound of the formula (4), in the inert solvent.

Examples of the, inert solvent can be used in this reaction are ethers such as diethyl ether, tetrahydrofuran, dioxane or the like; halogenated hydrocarbons such as dichloromethane, dichloroethane, chloroform, carbon tetrachloride or the like; aromatic hydrocarbons such as benzene, toluene, xylene or the like, and so on.

The halide compound of the formula (4) and the compound of the formula (I-a) are present in a molar ratio of 1:1 to 1.5:1. This reaction is conducted at room temperature to 100° C., preferably at 50° C. to 80° C., and can be carried to completion in 2 hours to B hours.

Referring to the obtained compound of the formula

Reaction Scheme-5

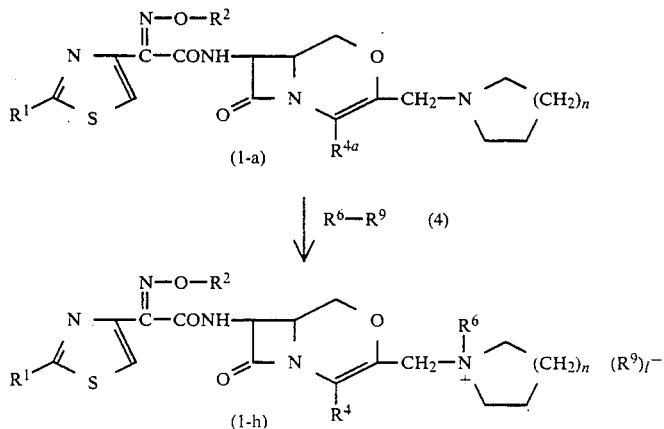

wherein $R^1$, $R^2$, $R^{4a}$, $R^4$, $R^9$, l, m and the group of the formula: and the group of the formula:

(1-h), when $R^1$ is the protected amino group, the compound having the amino group as $R^1$ is produced by elimination reaction of amino-protecting group. Anion, shown by $(R^9)^-$ can be exchanged to another anion by the anion exchange reaction.

Furthermore, referring to the compound of the formula (1-h), when $R^4$ is carboxyl group, after the completion of the reaction, the anion can be eliminated by purification of the column chromatography using Diaion HP-20(Mitsubishi Chemical Industries) or the like, so that the compound formed an inner salt, in which $R^4$ is carboxylate group and l means 0, can be produced.

When the anion is not eliminated, the compound whose $R^4$ is a carboxyl group as $R^4$ in the formula (1-a), is produced.

Referring to the compound of the formula (1-h), when $R^4$ means the esterified carboxyl group, the compound whose $R^4$ means alkoxy group is produced by the above mentioned deesterification reaction. After the completion of the deesterification, the anion may be eliminated by purification of column chromatography using the ion exchange resin, so that the inner salt whose $R^4$ means carboxylate group can be produced.

Reaction Scheme-6

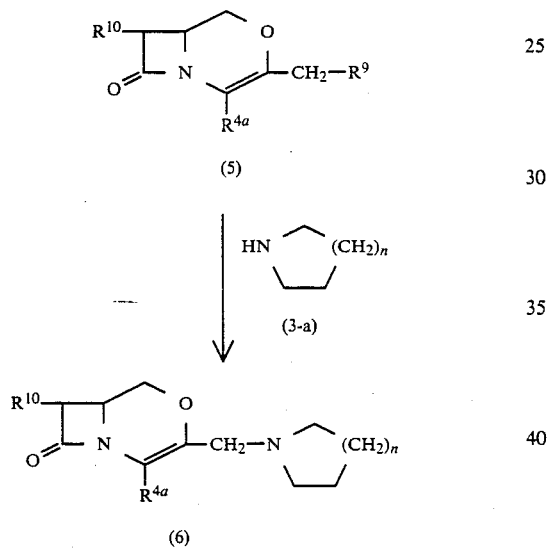

wherein $R^{4a}$, $R^9$, n and the group of the formula:

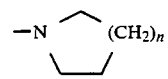

and the compound of the formula:

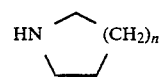

have the same meanings as defined above.

$R^{10}$ is azide group, phthalimide group which may have nitro group as a substituent group on the phenyl ring, amino group which may have a phenylaceticamide group or protecting group.

The reaction between the compound of the formula (5) and the Compound of the formula (3-a) is carried out in the same condition as the reaction between the compound of the formula (2) and the compound of the formula [3-a) in the above Reaction Scheme-1.

Reaction Scheme-7

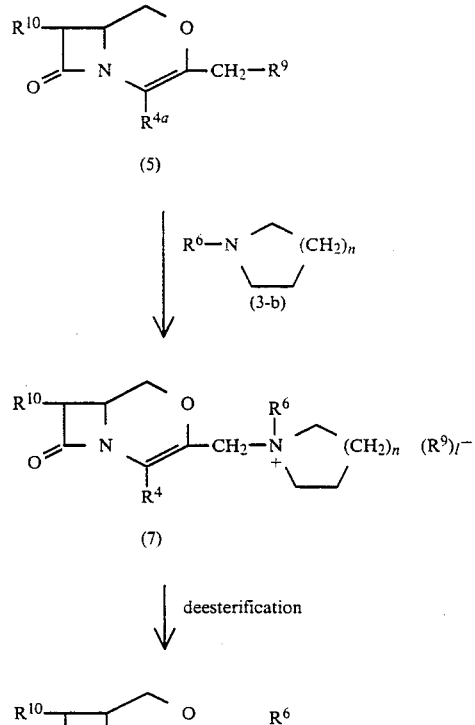

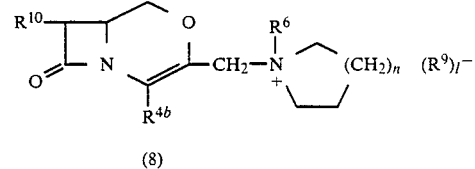

wherein $R^4$, $R^{4a}$, $R^{4b}$, $R^6$, $R^9$, $R^{10}$, l, n and the group of the formula:

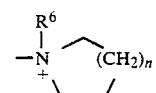

and the compound of formula:

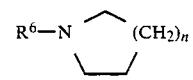

have the same meanings as defined above; and when $R^4$ is carboxyl group or esterified carboxyl group, or when $R^{4b}$ is carboxyl group, l is 1, when $R^4$ or $R^{4b}$ is carboxylate group, l is 0.

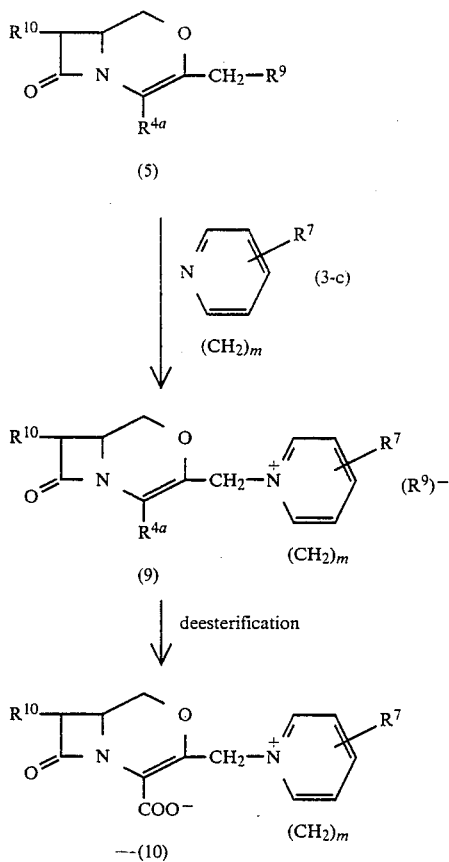

(5)

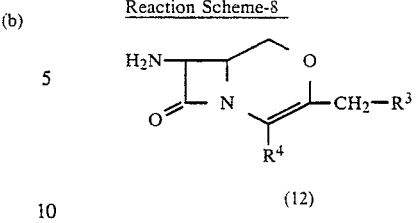
(3-c)

(9)

↓ deesterification

—(10)

wherein $R^{4a}$, $R^7$, $R^9$, $R^{10}$ and m have the same meanings as defined above.

The reaction between the compound of the formula (5) and formula (3-b) or (3-c) is carried out in the same condition as the reaction between the compound of the formula (3-a) and the compound of the formula (2) in the Reaction Scheme-1.

Referring to the obtained compounds of the formulas (7) and (9), when $R^4$ and $R^{4a}$ are esterified carboxyl groups, the compounds of the formulas (8) and (10) are respectively obtained by deesterification reaction of the compounds of the formulas (7) and (9). This deesterification can be carried out in the same condition as the deesterification of the Reaction Scheme-1.

Reaction Scheme-8

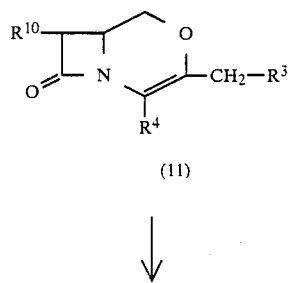

(11)

↓

-continued

Reaction Scheme-8

(12)

wherein $R^3$, $R^4$ and $R^{10}$ have the same meanings as defined above.

This Reaction Scheme-8 is the method for producing the compound of the formula (12) which includes compounds structurally different from the conventional compound, by conducting hydrolysis, reduction or hydrazine-decomposition in the compliance with the kind of $R^{10}$.

Referring to the above mentioned Reaction Scheme-8, the amine compound of the formula (12) is produced by permitting a reducing agent to act on the compound of the formula (II) in the absence of e solvent or in the presense of a suitable inert solvent.

As examples of the solvent to be used in this reaction, there is mentioned halogenated hydrocarbons such as dichloromethane, dichloroethane, chloroform, carbon tetrachloride or the like, aromatic hydrocarbons such as benzene, toluene, xylene or the like, ethers such as diethyl ether, tetrahydrofuran, dioxane or the like, and amines such as triethylamine, pYridine or the like.

As examples of the reducing agent, there is mentioned hydrogen sulfide or the like. When hydrogen sulfide is employed, it is preferable to add an amine such as triethylamine, pyridine or the like.

The reducing agent and the compound of the formula (2) are present in a molar ratio of 1:1 to 100:1 and preferably 3:1 to 50:1. This reaction is conducted generally at −30° C. to 50° C. and preferably at −10° C. to 10° C., and completed in about 30 minutes to 10 hours.

When is phenylacetic amide group, the amine compound of the formula (12) can be obtained by hydrolysis reaction of the compound of the formula (11), in the absence of a solvent or in the presence of an inert solvent. This hydrolysis reaction can be carried out in substantially the same condition as the deesterification in Reaction Scheme-1.

When $R^{10}$ is phthalimide group which may have a nitro group on phenyl ring as a substituent group, the amine compound of the formula (12) can be obtained by hydrazine-decomposition reaction between the compound of the formula (11) end hydrazine or hydrazine derivative in the absence of a solvent or in the presence of a suitable inert solvent.

The examples of the inert solvent to be used in this reaction are halogenated hydrocarbons such as dichloromethane, dichloroethane, chloroform, carbon tetrachloride or the like; alcohols such as methanol, ethanol, propanol or the like, and so on. The examples of hydrazine derivative are hydrazine substituted with lower alkyl group such as methylhydrazine, ethylhyhydrazine or the like, and hydrazine substituted with aryl group such as phenyl hydrazine, and so on.

The hydrazine compound or derivative thereof and the compound of the formula (11) are present in a molar ratio of 1:1 at least and preferably 1:1 to 2:1. This reaction is conducted generally at 0° C. to 100° C. and preferably at 0° C. to 80° C., and completed in about 1 to 40 hours.

When $R^{10}$ is the protected amino group, this reaction can be carried out in the same condition as the above mentioned elimination reaction of amino protecting group.

Reaction Scheme-9

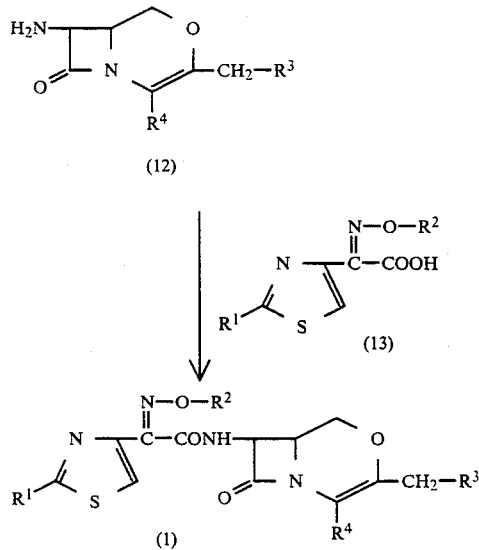

wherein $R^1$, $R^2$, $R^3$ and $R^4$ have the same meanings as defined above.

The compound of the formula (1) can be produced by reacting the amine compound of the formula (12) with a carboxylic acid compound of the formula (13) or a compound having an activated carboxyl group in the same condition as a conventional reaction for forming amide bond. This amide bond-forming reaction can be carried out by any of the known methods. The examples of the amide bond-forming reaction are explained below.

(a) The method involving the use of a condensing agent, wherein the carboxylic acid compound of the formula (13) is reacted with the amine compound of the formula (12) in the presence of a condensing agent.

(b) The mixed acid anhydride method, wherein the carboxylic acid compoundof hte formula (13) is reacted with an alkyl halocarboxylate to give a mixed acid anhydride, which is then reacted wi&h the amine compound of the formula (12).

(c) The activate ester method, wherein the carboxylic acid compound of the formula (13) is esterified into an active ester such as p-nitrophenyl ester, N-hydroxysuccinimide ester, 1-hydroxybenzotriazole ester or the like, which is then reacted with the amine compound of the formula (12).

(d) The method in which the carboxylic acid compound of the formula (13) is treated with a dehydrating agent such as acetic anhydride to give a carboxylic acid anhydride, which is then reacted with the amine compound of the formula (12).

(e) The method in which a $C_1$-$C_6$ alcohol ester of the carboxylic acid compound of the formula (13) is reacted with the amine compound of the formula (12) at elevated temperature and pressure.

(f) The method in which the carboxylic acid compound of the formula (I3) is converted to an acid halide, i.e. a carboxylic acid halide, which is then reacted with the amine compound of the formula (12).

An example of the amide bond-forming reaction is specifically described below.

The compound of the formula (I) according t ⓒ&he present invention can be obtained by reacting an amine compound of &he formula (I2) with a carboxylic acid compound of the formula (I3) in the presense of a condensing agent, either in &he absence of a solvent or in the presence of an inert solvent.

The examples of the condensing agent which can be employed in this reaction are dionyl chloride, phosphorus oxychloride, phosphorus pentachloride yilomcier reagent, dicyclohexylcarbodiimide (DCC), 2,2'-pyridinyl disulfide-triphenylphosphine, and so on.

As examples of the solvent, there may be mentioned any solvent which does not adversely influence the reaction, for example, ethers such as diethyl ether, tetrahydrofuran dioxane or the like; halogenated hydrocarbons such as dichlorome&hane, dichloroethane, chloroform, carbon etrachloride or the like; aromatic hydrocarbons such as benzene, toluene, xylene or the like; amines such as pyridine, piperidine, triethylamine or the like; aliphatic hydrocarbons such as hexane, heptane or the like; alcohols such as methanol, ethanol, propanol or the like; arctic polar solvents such as dimethylformamid, (DMF), hexamethylphosphoric triamide (HMPA), dimethyl sulfoxide (DMSo) or the like; and carbon disulfide.

The above reaction is preferably carried out in the presence of a basic compound. As examples of such basic compound, there may be mentioned organic bases such as triethylamine (e.g. trie&hylamine, tributylamine or the like), pyridine, picoline, I,5-diazabicyclo-[4,3,0]nonene-5, 1,4-diazabicyclo[2,2,2]octane, 1,8diazabicyclo-[5,4,0]undecene-7; and inorganic bases such as alkali metal hydroxides, e.g. monotrimethylsilylacetamide, sodium hydroxide, potassium hydroxide or the like, alkali metal carbonates, e.g. sodium carbonate, potassium carbonate or the like, alkali metal hydrogen carbonates, e.g. sodium hydrogen carbonate, potassium hydrogen carbonate and so on.

In the above reaction, the carboxylic acid compound of the formula (13) and the amine compound of the formula (12) are present in a molar ratio of 1:1 to 10:1 and preferably 1:1 to 3:1. The basic compound and the amine compound of the formula (12) are present in a molar ratio of 1:1 to 40:1 and preferably 5:1 to 20:1.

The above reaction is conducted at −20° C. to 100° C., preferably −20° C. to 50° C., for 30 minutes to 24 hours, preferably 30 minutes to 10 hours.

Referring to the above reaction between the amine compound of the formula (12) and the carboxylic acid compound of the formula (13), when the group $R^4$ is a carboxylate group, there maY be obtained, in certain cases, a compound such that the carboxyl group of the compound of the formula (1) is condensed with the amino group of the amine compound of the formula (12). In such cases, the compound of the formula (1) can be produced by hydrolyzing the condensation product compound in the presence of an acid catalyst such as an inorganic or organic acid, e.g. hydrochloric acid, hydrobromic acid, trifluoroacetic acid or the like.

Reaction Scheme-10

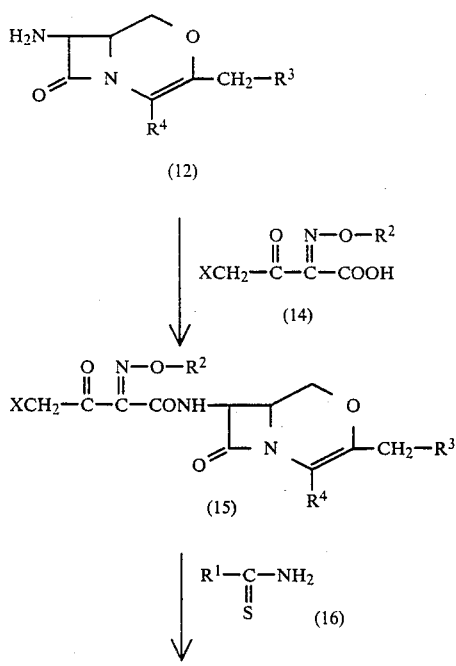

Referring to the above compound of the formula (14), halogen atom represented at X is chlorine atom, bromine atom, iodine atom and fluorine atom.

The reaction can be conducted in the same manner as the above mentioned amide bond forming reaction between amine compound of the formula (12) and carboxylic acid compound of the formula (13) in the Reaction Sheme-9.

The obtained compound of the formula (15) is then reacted with a thioacetoamido compound of the formula (16) in &he absence of a solvent or in the presence of a suitable inert solvent to give the compound of the formula (1) according to the present invention.

As the inert solvent used in this reaction, the same solvent as used in the Reaction Scheme-9 can be used.

In the above reaction, the compound of the formula (15) and the thioacetamido compound of the formula (16) are present in a molar ratio of 1:1 to 1:10 and preferably 1:1 to 1:5.

The above reaction is conducted at $-10°$ C. to $100°$ C. preferably $-10°$ C. to $50°$ C., for 1 to 50 hours, preferably 1 to 10 hours.

The compound of the formula (2) includes partially the new compound structurally different from the conventional compounds. For example, the new compounds are produced from the known compound by the method shown in the following Reaction Scheme-11.

Reaction Scheme-11

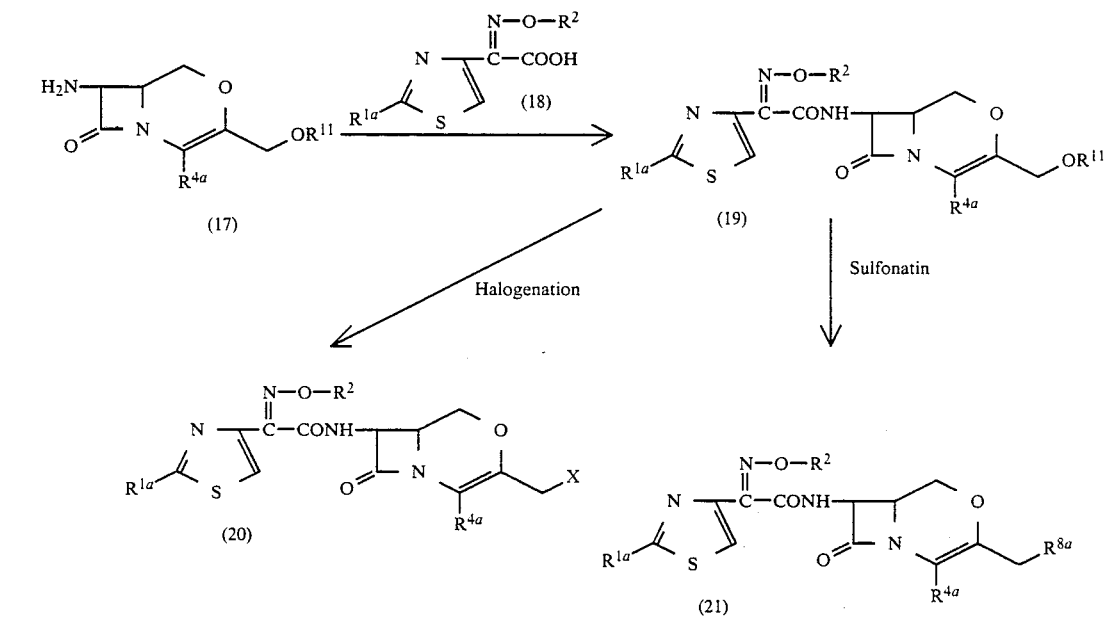

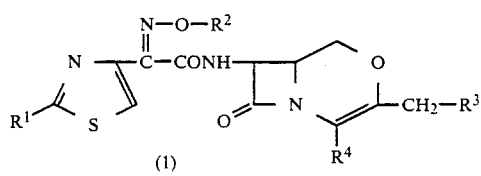

wherein $R^1$, $R^2$, $R^3$ and $R^4$ have the same meanings as defined above, and X is halogen atom.

Referring to the above reaction, the compound of the formula (15) can be obtained by the reaction between amine compound of the formula (12) and carboxylic acid compound of the formula (14).

wherein $R^2$, $R^{4a}$ and X have the same meanings as defined above. $R^{9a}$ is the same meanings as $R^9$ except for halogen atom, $R^{1a}$ is protected amino group and, $R^{11}$ is hydrogen atom or $C_1$-$C_6$ alkanyl group.

The reaction between the compound of the formula (17) and the compound of the formula (18) can be conducted in the same manner as the above mentioned reaction between the compound of the formula (12) and the compound of the formula (13) in the Reaction Scheme-9.

The halogenaition reaction for obtaining the compound of the formula (20) from the compound of the formula (19) is one that alcoholic hydroxy group or lower alkanoyloxy group is substituted with halogen atom, and therefore the condition of the usual halogenaition can be applied.

For example, when $R^{11}$ is hydrogen atom, the compound of the formula (20) is obtained by the reaction of the compound of the formula (19) with halogenated thionyl, such as chloro thionyl, bromo thionyl, iodo thionyl in the absence of a solvent or in the presence of a suitable inert solvent.

As examples of the solvent, there may be mentioned any solvent which does not adversely influence the reaction, for example, ethers such as diethyl ether, tetrahydrofuran, dioxane or the like; halogenated hydrocarbons such as dichloromethane, dichloroethane, chloroform, carbon tetrachloride or the like; aromatic hydrocarbons such as benzene, toluene, xylene or the like; amines such as pyridine, piperidine, triethylamine or the like; aliphatic hydrocarbons such as hexane, heptane or the like; alcohols such as methanol, ethanol, propanol or the like; aprotic polar solvents such as dimethylformamide (DMF), hexamethylphosphoric triamide (HMPA), dimethyl sulfoxide (DMSO) or the like; and carbon disulfide, and so on.

In the above reaction, the compound of the formula (19) and the halogenated thionyl are present in a molar ratio of 1:1 at least and preferably 1:1 to 1:2. The reaction is conducted at $-10°$ C. to room temperature and preferably under ice-cooling, for 5 minutes to 1 hour.

To this reaction system, preferably, the basic compound, such as pyridine, dimethylaniline, triethylamine or the like, may be added as an acid-catching agent.

When $R^{11}$ is lower alkanoyl group, the compound of the formula (20) can be obtained by reacting tri(lower alkyl)silylhalide with the compound of formula (19) in the absence of solvent or in the presence of suitable inert solvent.

As a solvent used in this reaction, the above mentioned solvent can be employed. For example, tri(lower alkyl)cyclohalaide, trimethylcylylchloride, triethylsilylchloride or the like, can be employed.

In the above reaction, the compound of the formula (19) and tri(lower alkyl)silylhalaide are present in a molar ratio of 1:1 at least and preferably 1:1 to 1:2.

The above reaction is conducted at $-20°$ C. to 50° C., and preferably room temperature, for 30 minutes to 5 hours.

The sulfonation reaction for obtaining the compound of the formula (21) from the compound of the formula (19) is carried out by &he reaction between the compound of the formula (19) and sulfonic acid compound or the reactive derivative thereof in the absence of a solvent or in the presence of an innert solvent.

As examples of the inert solvent, there is mentioned ethers such as diethyl ether, tetrahydrofuran, dioxane or the like; halogenated hydrocarbons such as dichloromethane, dichloroethane, chloroform, carbon tetrachloride or the like; aliphatic hydrocarbons such as hexane, heptane, octane or the like.

As examples of the sulfonic acid compound there is mentioned lower alkanesulfonic acid such as methanesulfonic acid, ethanesulfonic acid, propansulfonic acid or the like; or arylsulfonic acid having 1 to 3 substituent groups selected from the group consisting of $C_1$-$C_6$ alkYl group, halogen atom and nitorogen atom, such as benzenesulfonic acid, toluenesulfonic acid, p-chlorobenzenesulfonic acid, p-nitorobenzenesulfonic acid or the like. As examples of the reactive derivative of sulfonic acid, there is mentioned halogenated sulfonic acid, such as sulfochloride, sulfobromide, sulfonic acid anhydride, or the like.

In the above reaction, &he compound of the formula (19) and the above mentioned sulfonic acid compound or the reacted derivative thereof are present in a molar ratio of 1:1 at least and preferably 1:1 to 1:1.5. The above reaction is conducted at $-50°$ C. to icecooling temperature for 1 minutes to 50 minutes.

This reaction can also conducted in the presence of the acid-catching agent, such as pyridine, triethylamine, and preferablY, after completion of the reaction, the acid-catching agent was added to react for 30 minutes to 3 hours, preferably about I hour. The acid-catching agent and the reactive derivative of sulfonic acid compound or the reactive derivative of sulfonic acid are present in a molar ratio of 1:1 at least and preferably 1:1 to 1.5:1.

The obtained compounds of the formulas (20) and (21) can be conducted into the corresponding amino compounds by elimination reaction of the amino-protecting group of $R^{1a}$ under the same condition as the above mentioned elimination reaction of the amino-protecting group. Also, when $R^{4a}$ is esterified carboxyl group, the obtained compound of the formula (20) and (21) can be conducted into the corresponding carboxyl compounds by deesterification reaction under the same condition of the above mentioned deesterification reaction. Further, the compounds of the formulas (20) and (21) can be conducted into the corresponding compounds having carboxyl group and amino group by both deesterification reaction of $R^{4a}$ and elimination of amino-protecting group of $R^1$.

Among the compounds of general formula (1) according to the present invention, compounds having basic groups can be easily converted to salts by permitting a pharmaceutically acceptable acid to act thereon, while compounds having acidic groups can be easily converted to salts by reacting them with a pharmaceutically acceptable basic compound. The acid is exemplified by inorganic acids such as hydrochloric acid, sulfuric acid, phosphoric acid, hydrobromic acid or the like; and organic acids such as oxalic acid, maleic acid, fumaric acid, malic acid, tartaric acid, citric acid, benzoic acid, acetic acid, p-toluenesulfonic acid, ethanesulfonic acid or the like. The basic compound is exemplified by metal hydroxides such as sodium hydroxide, potassium hYdroxide, calcium hydroxide or the like and alkali metal carbonates or alkali metal hydrogen carbonates such as sodium carbonate, sodium hydrogen carbonate, potassium hydrogen carbonate or the like. The salts of the compound of the invention naturally includes inner salts.

The produced compound of the present invention can be isolated and purified without difficulty by conventional means of separation. Employable as the conventional means of separation are, for instance, solvent extraction, dilution, recrystallization, column chromatography and preparative thin layer chromatography.

The compound of the invention as represented by general formula (1) naturally includes optical isomers as well as syn and anti isomers. These isomers can be separated from each other by a conventional resolution method, for example, by using an optical resolution agent or an enzyme.

The compounds of this invention as therapeutic agents, these compounds can be formulated into pharmaceutical compositions together with ordinary pharmaceutically acceptable carriers. Suitable carriers which can be used are, for example, solvents, or excipients such as fillers, extenders, binders, wetting agents, disintegrants, surface active agents and lubricants which are usually employed to prepare such drugs depending on the type of dosage form.

Various dosage forms of the therapeutic agents can be selected according to the purpose of the therapy. Typical dosage forms which can be used are tablets, pills, powders, liquid preparations, suspensions, emulsions, granules, capsules, suppositories, and injectable preparations (solutions, suspensions or the like).

In molding a pharmaceutical composition into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethyl cellulose, shellac, methyl cellulose, potassium phosphate and polyvinyl pyrrolidone, diaintegrants such as dried starch, sodium alginate, agar powder, laminaria powder, sodium hydrogen-carbonate, calcium carbonate, polyoxyethylenesorbitan fatty acid esters, sodium laurylsulfate, stearic acid monoglyceride, starch, and lactose, disintegration inhibitors such as white sugar, stearin, cacao butter and hydrogenated oils, absorption promotors such as quaternary ammonium bases and sodium laurylsulfate, humectants such as glycerol and s&arch, adsorbents such as starch, lactose, kaolin, bentonite and colloidal silicic acid, and lubricants such as purified talc, stearic acid salts. boric acid powder, polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, end semisynthetic glycerides.

When the pharmaceutical composition is formulated into an injectable preparation, the resulting solution and suspension are preferablY sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxylated isostearyl alcohol, and polyoxyethylenesorbitan fatty acid esters. Sodium chloride, glucose or glycerol may be incorporated into a pharmaceutical composition, in an amount sufficient to prepare isotonic solutions. The pharmaceutical composition may further contain ordinary dissolving aids, buffers, pain alleviating agents, and preservatives, and optionally coloring agents, perfumes, flavors, sweeteners and other drugs.

In molding a pharmaceutical composition into an ointment form, a cream form and a gel form, a wide range of diluents known in the arts can be used. Examples of suitable diluents include white petrolatum, paraffin, glycerin, cellulose derivatives, polyethylene glycol, silicones, and bentonite.

The amount of the compound of the formula (1) and the pharmaceutically acceptable salts thereof of this invention as an active ingredient to be incorporated into a pharmaceutical composition is not particularly limited, and can very over a wide range. A suitable therapeutically effective amount of the compound of the general formula (I) and the pharmaceutically acceptable salts thereof of this invention is usually about 1 to about 70% by weight, based on the entire composition.

The administration method of the pharmaceutical composition according to the invention is not particularly limited and can be adequately selected according to the form of the preparation, age and sex of the patient, and symptom of disease. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the injectable preparations can be singly administered intra muscularly, intracutaneously, subcutaneously, or in-traperitaneally. The suppository is administered intrarectally.

The dosage of the pharmaceutical composition is suitably selected according to the purpose of use, age and sex of the patient, and the symptoms of disease or the like. Usually, a preferred dosage of the compound of this invention is about 1100 mg/kg, preferably 5 to 20 mg/kg weight per day, and the pharmaceutical composition may be administered 2 to 4 times per day.

EXAMPLES

Hereinafter, this invention will be described in greater detail with reference to Reference Examples and Examples.

Reference Example 1

Diphenylmethyl (6S,7S)-7-azido-3-(1pyrrolidinYl)methyl-$\Delta^3$-0-2-isocephem-4-carboxylate Diphenylmethyl (6S,7S)-7-azido-3-iodomethyl-$\Delta^3$-0-2-isocephem-4-carboxylate (2 g) was dissolved in methylene chloride (20 ml}, followed by addition of pyrrolidine (0.39 ml). The reaction was conducted at room temperature for 3 days. After washing the reaction mixture with the solution of 0.5M citric acid, saturated aqueous solution of sodium hydrogencarbonate and saturated aqueous solution of saturated sodium chloride, the mixture was dried over by magnesium sulfate anhydride. After filtrating, the filtrate was concentrated under reduced pressure, and residue was separated and purified by silica gel column chromatography [eluent: chloroform]to give the title compound (0.7g).

NMR (CDCl$_3$)δ:
1.6–1.9 (4H, m), 2.3–2.7 (4H, m), 3.6–4.2 (4H, m), 4.63 (1H, dd), 5.20 (1H, d), 6.84 (1H, s), 7.0–7.6,(10H, m).

Reference Example 2

Diphenylmethyl (6S,7S)-7-azido-3-1,2,3,4-tetrahydroisoquinol-2-yl)methyl-Δ³-O-2-isocephem-4-carboxylate Diphenylmethyl (6S,7S)-7-azido-3-iodomethyl-Δ³-O-2-isocephem-4-carboxylate (1.90 g) was dissolved in methylene chloride (60 ml), followed by addition of 1,2,3,4-tetrahydroisoquinoline (1.20g). The reaction was conducted at room temperature for 6 hours. After washing the reaction mixture with water and with saturated aqueous sodium chloride in turn, the mixture was dried over by sodium sulfate anhydride. After concentrating the solvent, the residue was separated and purified by silica gel column chromatography [eluent: n-hexane:ethyl acetate (3:2)] to give the title compound (1.53g) as a white solid.

NMR (CDCl₃) δ: 6.90–7.59 (15H, m), 5.22 (1H, d, J=12Hz, 4Hz), 3.6–4.07 (6H, m), 2.78 (4H, bs).

Reference Example 3

Benzhydryl (6S,7S)-7-[2-(2-tritylaminothiazol-4-yl-2-methoxyiminoacetamido]-3-{hydroxY)methYl-Δ³-O-2-isocephem-4-carboxylate (syn isomer)

2-(2-tritylaminothiazol-4-yl)-2-methoxyiminoacetic acid (syn isomer) (4.82 g) was dissolved in methylene chloride (100 ml), followed by addition of 1-hydroxybenzotriazole (HoBT) (1.46g), dicyclohexylbenzotriazole (DCC) (2.24g), and stirred for 30 minutes under ice-cooling. After stirring, to the reaction mixture was added benzhydoryl (6S,7S)-7-amino-3-hydroxymethyl-Δ³-O-2-isocephem-4-carboxylate (3.74g). The reaction was conducted at room temperature for 18 hours. Thereafter, the reaction mixture was filtrated, and the filtrate was concentrated for drYing. Residue was purified bY silica gel column chromatography [eluent: n-hexane:chloroform (1:5)] to give the title compound (0.7g) as a white crystal.

mp : 181–182° C.

Reference Example 4

Benzhydryl {6S.?S}-7-[2-(2-tritylaminothiazol-4-yl)-2-methoxyiminoacetamide]-3-methanesulfonyloxymethyl-Δ³O-2-isocephem-4-carboxYlate (syn isomer)

The compound of the Reference Example 3 (1.00g) was dissolved in methylene chloride (20 ml), followed by addition of triethylamine (0.19ml) and then of methylene chloride solution (5ml) of methanesulfonylchloride (0.16 g), and stirred under cooling of ice-sodium chloride. The reaction mixture was washed with 0.5N hydrochloric acid, and saturated aqueous solution of sodium chloride, dried over bY magnesium sulfate, and solvent was removed. The residue was re-sedimented from methylenechloride-n-hexane to give the title compound (1.02 g) as a white powder.

mp : 141° C. (colored, perfectly changing to brown oil at 153° C.)

Example 1

Diphenylmethyl (6S,7S)-7-[2-(2-tritylaminothiazol-4-yl)-2-methoxyiminoacetamide]-3-(1-pyrrolidinyl)methyl-Δ³-O-2-isocephem-4-carboxylate (syn-isomer)

The compound of the Reference Example 1 ( 0.7 g) was dissolved in methylene chloride (50 ml), followed by addition of tritylamine (0.3 ml). After passing hydrogen sulfide gas for 10 minutes under ice-cooling, the reaction was conducted at room temperature for 2 hours. Thereafter, the reaction mixture was washed with the aqueous solution of sodium hydrogencarbonate and the aqueous solution of sodium chloride, dried over by magnesium sulfate anhydride. After filtering, the filtrate was concentrated, and added to the reaction mixture which is previously produced by reacting 2-(2-tritylaminothiazol-4-yl)-2-methoxyiminoacetic acid (syn isomer) (0.74 g) with dicyclohexyl-carbodiimido (DCC) (0.35 g) and 1-hydroxybenzotriazole (HoBT) (0.23 g) for 1 hour under ice-cooling. The reaction was conducted for 17 hours in room temperature. After filtering, the filtrate was concentrated, and gas purified and separated by silica gel column chromatography. [eluent: chloroform:methanol (50:1)] to give the title compound (0.75g).

NMR (CDCl₃)δ:
1.8–2.2 (4H, m}, 3.0–4.6 (12H, m including 3.75, 3H, s]), 5.76 (1H, dd), 6.59 (1H, s), 6.70 (1H, s), 6.9–7.7, (25H, m), 8.59 (1H, d).

Example 2

(6S,7)-7-[2-(2-aminothiazol-4-Yl-2-methoxyiminoacetamido]-3-(i-pyrrolidinYl)methyl-Δ³-O-2-isocephem-4-carboxylic acid trifluoroacetate (syn isomer)

To the title compound of Example ! (0.4g) was added 60% acetic acid (4ml), and after reacting at 40° C. for 1 hour, was concentrated. After enoughly drying under reduced pressure, to the reaction mixture was added anisole (o.4ml) and trifluoroacetic acid (4 ml), and was reacted for 10 minutes under ice cooling, followed by addition diethyl ether. The deposited solid was filtrated and dried to give the title compound (0.14 g).

mp:120° C.(color change)

NMR (DoMS-d6)δ: 1.7–2.2 (4H, m}, 3.0–3.6 (4H, m), 3.8–5.0 (8H, m. including 3.75, 3H, s), 5.76 (1H, dd), 6.80 (1H, s), 9.19(1H, d).

Example 3

(6S,7S)-7-[2-(2-aminothiazol-4-yl)-2-methoxyiminoacetamide-3-(1-methyl-1-pyrrolidinio)methyl-Δ³-O-2-isocephem-4-Carboxylate (syn isomer)

Diphenylmethyl (6S,7S)-7-[2-(2-tritylaminothiazol-4-yl)-2-methoxyiminoacetamide]-3-sulfonyloxymethyl-4-carboxylate (syn isomer) (1g) was dissolved in methylene chloride (5ml), followed by addition of N-methylpyrrolidine (0.35ml). The reaction was conducted in room &temperature for 2 days. After repeating re-precipitation of the reaction mixture three times by methylene chloride and diethyl ether, and removing the supenatant solution by decantation, the precipitate was dried over.

To the product was added 60% acetic acid (20 ml), and after reacting at 40° C. for 1 hour, was concentrated. After drying, in the presence of anisole (1 ml), the reaction mixture was reacted with trifluoroacetic acid (10 ml) under ice-cooling for 10 minutes. Then, to the reaction mixture was added diethyl ether, and the deposited solid was obtained by filtration. This solid was dissolved in water again, and a nonionic adsorbent resin Diaion HP-20 (25g) was added to absorb the solid under the condition of pH 4 adjusted by sodium hydrogencarbonate The absorbed resin was filled in a column, washing with water, was eluted by 5% aqueous solution of isopropanol. The eluent was concentrated, and precipitated by methanol-diethyl ether. The precipitate was filtrated to give the title compound (0.22g).

mp:160° C.(color change)

NMR (DoMS-d6)δ: 1.8-2.3 (4H, m), 3.03 (3H, m), 3.2-4.8 (12H, m including 3.85, 3H, s), 5.59 (1H, dd), 6.78 (1H, s), 7.18(2H, bs), 9.23(1H,, d).

Example 4

(6S,7S)-7-[2-(2-aminothiazol-4-yl)-2-isopropyloxyiminoacetamido]-3-(1-methyl-1pyrrolidinyomethyl-Δ³-0-2-isocephem-4-carboxylate (syn somer)

In a manner analogous to Example 3, the title compound was produced from the suitable starting compound.

mp: 167° C. (color change)

Example 5

(6S,7S)-7-[2-2-aminothiazol-4-yl-2cyclopentyloxyiminoacetamide]-3-(1-methyl-1-pyrrolidinyo)methyl-Δ³-0-2-isocephem-4-carboxylate (syn-isomer)

In a manner analogous to Example 3, the title compound was produced from the suitable starting compound.

mp: 159° C. (color change)

Example 6

(6S,7S)-7-[2-(2-aminothiazol-4-yl)-2-cyclopentyloxyiminoacetamide]-3-(1-methyl-1-pyrrolidinyo)methyl-Δ³-0-2-isocephem-4-carboxylate (syn isomer)

In a manner analogous to Example 3, the title compound was produced from the suitable starting compound.

mp: 147° C. (change color)

Example 7

Diphenylmethyl (6S,7S)-7-[2-(2-tritylaminothiazol-4-yl)-2-methoxyiminoacetamide]-3-(1,2,3,4-tetrahydroisoquinol-2-yl)methly-Δ³-0-2-isocephem-4-carboxylate (syn isomer)

The title compound of Reference Example 2 (1.08 g) was dissolved in methylene chloride (100 ml), followed by addition of triethylamine (0.35 ml). Under ice-cooling, hydrogen sulfide gas was introduced into the mixture. After confirming the disappearance of the starting compound and production of the amine on TLC, the reaction mixture was washed with 1% aqueous solution of sodium hydrogen carbonate and aqueous solution of sodium saturated sodium chloride in turn. The mixture was dried over by anhydrous magnesium sulfate, and filtrated. To the filtrate was added 2-(2-tritylaminothiazol-4-yl)-2-methoxyiminoacetic acid (syn isomer) (1.95g), and after cooling in ice both, added dicuyclohexylcarbodiimide (0.93g), and 1-hydroxybenzotriazole (0.20g). Then, the mixture was stirred over night at room temperature. After filtering off the deposit, the filtrate was concentrated, the residue was dissolved in ethylacetate, and the mixture was filtrated to separate an indissolved material. The filtrate was washed with the water, the saturated aqueous solution of sodium hydrogen carbonate and saturated aqueous solution of sodium chloride in this order, dried over by anhYdrous magnesium salfate, and filtrated. The filtrate was concentrated. The residue was subjected to silica gel column chromatography (eluent: chloroform) for separation and purification to give the title compound (1.85g) as a tiny-Yellow solid.

mp: gradually changing color from near 152° C.

NMR (CDCl₃)δ: 6.72-7.56 (32H, m), 6.58 (IH, s ), 5.49 (1H, dd, J=5Hz, 4Hz), 4.66 (2H, dd, J=13Hz, 8Hz), 3.76-4.07 and 4.01 (m,s, total 6H), 3.64 (2H, bs), 2.78(4H, bs).

Example 8

(6S,7S)-7-[2-(2-aminothiazol-4-yl)-2-methoxyiminoacetamide]-3-(1,2,3,4-tetrahydroquinolyn-2-yl)methyl-Δ³-0-2-isocephem-4-carboxylic acid (syn isomer)

The compound of Example 7 (0.70 g) was dissolved in acetic acid (20 ml), followed by addition of water (10 mlj. After stirring at 40° C. for 2 hours, the solvent was distilled off under reduced pressure. To the residue was added methanol (20ml), and the solvent was distilled off under reduced pressure. The residue was reacted in trifluoro acetic acid in the presence of anisole (1 ml) for 7 minutes under ice-cooling. Then, diethyl ether (50ml) was added, and the resulting solid was isolated. The solid was washed with diethyl ether and dried over to give the trifluoroacetate of the titled compound (0.32g). The compound was dissolved in 5% aqueous solution of sodium hydrogen-carbonate and the nonionic absorbent resin Diaion HP-20 was added, followed bY adjusting to pH 3.4 by IN hydrochloric acid. The resin was filled in a column, and dissolved by the mixed solvent of water-isopropYl alcohol, and to the intended compound was eluted as 10% aqueous solution of isopropyl alcohol. The eluent was distilled away under reduced presser and freeze-dried to give the title compound (0.Q9g), as a light-brown powder.

NMR {DoMS-d6)δ: 9.07 (1H, d, J=9Hz), 7.1I (6H, bs), 6.79 (1H, s), 5.66 (1H,dd, J=9Hz, 4Hz), 4.53 (2H, dd, J=14Hz, 8Hz), 3.83 and 8.25-3.96 m, s, total 8H), 2.85 (4H, bs)

Example 9

(6S,7S)-7-[2-(2-aminothiazol-4-yl)-2-methoxyiminoacetamide]-3-(2-methyl-2-1,2,3,4tetrahydroisoquinoline)methyl-Δ³-0-2-isocephem-4-carboxylate (syn isomer)

The compound obtained in Example 7 (0.85 g) was stirred in the mixed solvent of methyl iodide (10ml) and methanol (10 ml) overnight. After distilling the solvent away, diethyl ether was added to solidifY as a yellow solid of the tertiary salt. In the same manner of Example 8, the mixture was treated with acetic acid-water, anisole-tritylfluoroacetic acid in this order to give trifluoroacetate of the titled compound. Further, to the nonionic absorbent resin Diaion HP-20 was absorbed the compound at pH 2.5, and the resin was filled in a column, followed by elutting as 10% aquerous solution of isopropyl alcohol. The eluent was concentrated and then freeze-dried to give the title compound (0.14g).

mp : color change at near 177° C.

NMR (DoMS-d6)δ: 9.12 (1H, d, J=9Hz), 7.02-7.26 (6H, m), 6.76 (1H, m), 5.56 (IH, dd, J=9Hz, 4Hz), 4.60-4.94 (2H, m), 3.83 and 3.65-3.94 (s and m, total 8H), 3.09 (4H, bs), 2.37 (3H, s)

Example 10

Benzhydryl (6S,7S}-7-[2-(2-tritylaminothiazol-4-yl-2-methoxyiminoacetamide-3-[(1-pyridinio)methyl]-Δ³-0-2-isocephem-4-carboxylate methanesulfonate (syn isomer)

Benzhydryl (6S,7S)-7-[2-(2-tritylaminothiazol-4-yl)-2-methoxyiminoacetamide]-3-methanesulfonyloxymethyl-0-2-isocephem-4-carboxylate (sYn-isomer) (0.60g) was dissolved in methylene chloride (10 ml), followed by addition of pyridine (0.16ml), and was reacted for 15 hours in room temperature. To the mixture was added diethylether (50ml), and the resulting solid is recovered by filtration to give the title compound (0.43g) colored to tiny yellow.

NMR (0DC13)δ: 2.67 (3H, s), 3.6–4.3 [5H, m including 4.02 (3H, s)], 4.49 (1H,dd), 5.76 (2H, ABq), 5.81 (1H, dd), 6.67 (1H, s), 7.0–7.5,(25H, m), 7.6–8.0 (2H, m), 8.0-8.4,(lH, m), 8.7–9.2(2H, m).

Example 11

(6S,7S)-7-[2-(2-aminothiazol-4-yl)-2-methoxyiminoacetamide-3-[(1-pyridinio)methyl]-Δ³-0-2-isocephem-4-carboxylate (syn isomer)

The compound obtained in Example 10 (0.38 g) was added to the mixture of acetic acid (6ml) and water (4 ml), and treated for 1 hour at 40° C. After distilling the solvent away, the residue was treated with trifluoroacetic acid (3ml) in the presence of anisole (0.3ml) for 10 minutes under ice-cooling, followed by addition of diethyl ether 5oml. And the solid gas obtained by filtration The solid was dissolved in Water (50 ml) and adjusted to pH 5 by the saturated aqueous solution of sodium hydrogen-carbonate. Then, the nonionic absorbent resin Diaion HP-20 (I5 g) was added, and after stirring for 10 minutes at room temperature, was filtrated to fill in a column. After passing water (300 ml) to the column, the elution was conducted by 2.5% aqueous solution of isopropyl alcohol. The fractions containing the objecting compound were collected and the solvent was distilled aWay. The residue was solidified by acetone, followed by filtrating, and thereby the title compound (0.04 g) of tiny red color gas obtained.

mp: 168° C. (changing to brown color)

NMR (CDCl₃) δ: 3.4–4.1 [5H, m, including 3.77 (3H, s)], 5 57 (1H, dd), 4.35 (1H, dd), 5.73 (2H, ABq), 6.68 (1H, s), 7.08 (2H, bs), 7.9–8.3 (2H, m), 8.4–8.7,(1H, m), 8.98 (1H, d), 9.28 (2H, d).

Example 12

(6S,7S)-7-[2-(2-aminothiazol-4-yl)-2isopropyloxyiminoacetamide]-3-[(1-pyridinio)methyl]-Δ³-0-2-isocephem-4-carboxylate (syn isomer)

In a manner analogous to Example 10, the title compound was produced from the suitable starting compound.

mp: 153° C. (color change)

Example 13

(6S,7S)-7-[2-(2-aminothiazol-4-yl)-2-cyclopentyloxYiminoacetamide]-3-[(1-pyridine)methyl]-Δ³-0-2-isocephem-4-carboxylate (syn isomer)

In a manner analogous to Example 11, the title compound was produced from the suitable starting compound.

mp: 161° C. (color change)

Example 14

(6S,7S)-7-[2-(2-aminothiazol-4-yl)-2methoxyiminoacetamide]-3-[(4-cyanomethylthio-1pyridinio)-methyl]-Δ³-0-2-isocephem-4-carboxylate (syn isomer)

Benzhydryl 6s,7s-7-12-(tritylaminothiezol-4-yl)-2-methoxyiminoacetamide-3-methanesulfonyloxymethyl-0-2-isocephem-4-carboxylate (syn-isomer) was dissolved in methylene chloride (20ml}, and 4-cyanomethylthiopyridine (0.51 g) was added. The mixture was stirred for 48 hours at room temperature, followed by addition of diethyl ether (80ml). The obtained solid was filtered and washed with diethyl ether The solid was added to the mixed solvent of acetic acid (30ml) and water (20ml), and was reacted for 2 hours at 40° C. After distilling the solution away, the residue was treated with trifluoroacetic acid (10ml) in the presence of anisole (0.3ml) for 10 minutes under ice-cooling, followed by addition of diethyl ether (80ml), and filtrated to obtain the produced solid. Then, the mixture was purified in the same manner as in Example 2 by the nonionic absorbent resin Diaion HP-20 to give the title compound (0.034g) of a tiny-red color.

m,p : 149° C. ( coloring to brown)

NMR (DMSo-d6)δ: 3.5–4.1 [5H, m, including 3.78 (3H, s)], 4.35 (1H, dd), 4.62 (2H, s), 5.56 (!H, dd), 5.60 (2H, ABq), 6.68 (1H, s), 7.07 (2H, bs), 8.05 (2H, d), 8.98 (1H, d), 9.14 (2H, d).

Example 15

(6S,7S)-7-[2-(2-aminothiazol-4-yl)-2methoxyiminoacetamide]-3-[[4-(3-pyrazolyl)-1-pyridinio]methyl]-Δ³-0-2-isocephem-4-carboxylate (syn isomer)

Benzhydryl (6S,7S)-7-[2-(2-tritylaminothiazol-4-yl)-2-methoxyiminoacetamide]-3-methanesulfonyloxymethyl-0-2-isocephem-4-carboxYlate (syn isomer) (1.00g) was reacted with 4-(I-tritylpyrazol-3-yl)pyridine (0.44g) in the same manner as in Example I4, to give the title compound (0.025 g) of light red color.

mp : 178° C. (changing in brown color)

NMR (DMSo-d6)δ: 3.5–4.1 [5H, m, including 3.78 (3H, s)], 4.34 (1H, dd), 5.55 (IH, dd), 5.68 {2H, ABq), 6.67 {1H, s}, 7.06 (1H, bs), 7.16 (1H, d), 7.92 (IH, d), 8 42 (IH, d), 8.98 (1H, d), 9.22 (2H, d)

Example 16

(6S,7S)-7-[2-(2-aminothiazol-4-yl)-2isopropyloxyiminoacetamide]-3-[[4-(5-oxazo]-yl)-1-pyridinio]methyl]-Δ³-0-2-isocephem-4-carboxylate (syn isomer)

In a manner analogous to Example 14, the title compound was produced by using 5-(4-pyridyl)oxazole.

m.p. : 165° C. (color change)

Example 17

(6S,7S)-7-[2-(2-aminothiazol-4-yl)-2-isopropyloxyiminoacetamide]-3-[(6,7-dihydro-5H-1-pyridinio)]methyl]-Δ³-0-2-isocephem-4-carboxylate (syn isomer)

In a manner analogous to Example 14, the title compound was produced from cyclopentenopyridine.

m.p : 158° C. (color change)

Example 18

(6S,7S)-7-[2-(2-aminothiazol-4-yl)-2-cyclopentyloxyiminoacetamide]-3-[[4-(5-oxazolyl)-1pyridinio]methyl]-Δ³-0-2-isocephem-4-carboxylate (syn isomer)

In a manner analogous to Example 14, the title compound was produced from the suitable starting compound.

m.p : 149° C. (color change)

Example 19

(6S,7S)-7-[2-(2-aminothiazol-4-yl)-2allyloxyiminoacetamide]-3-[[4-(6-oxazolYl)-1pyridinio]methyl]-$\Delta^3$-0-2-isocephem-4-carboxylate (syn isomer)

In a manner analogous to Example 14, the title compound was produced from the suitable starting compound.

m.p : 151° C. (color change)

| Pharmaceutical Example 1 | |
|---|---|
| (6S,7S)-7-[2-(2-aminothiazol-4-yl)-2-methoxyiminoacetamide]-3-(1-pyrrolidinyl)methyl-$\Delta^3$-0-2-isocephem-4-carboxylic acid (syn isomer) | 200 mg |
| Glucose | 250 mg |
| Distilled water for injection | q.s. |
| Total | 5 ml |

In Distilled water for injection are dissolved (6S,7S)-7-[2-(2-aminothiazol-4-yl)-2-methoxyiminoacetamide]-3-(1-pyrrolidinyl)methyl-$\Delta^3$-0-2-isocephem-4-carboxylic acid (syn isomer) and glucose, and the solution was filled into a 5 ml sample. After nitrogen purging, sterilization was carried out by autoclaving at 121° C. for 15 minutes to give a parenteral product of the above composition.

| Pharmaceutical Example 2 | |
|---|---|
| (6S,7S)-7-[2-(2-aminothiazol-4-yl)-2-methoxyiminoacetamide]-3-(1-methyl-1-pyridino)methyl-$\Delta^3$-0-2-isocephem-4-carboxylate (syn isomer) | 100 g |
| Avicel (trademark of Asahi Chemical Industry) | 40 g |
| Corn starch | 30 g |
| Magnesium stearate | 2 g |
| TC-5 (trademark of Shin-Etsu Chemical; hydroxypropylmethyl-cellulose) | 10 g |
| polyethylene glycol 6000 | 3 g |
| Castor oil | 40 g |
| Ethanol | 40 g |

(6S,7S)-7-[2-(2-aminothiazol-4-yl)-2-methoxyiminoacetamide]-3-(1-methyl-1-pyridinio)methyl-$\Delta^3$-0-2-isocephem-4-carboxylate (syn isomer), Avicel, corn starch and magnesium stearate were milled together and tableted by means of R 10 mm punch (for sugar-coated tablets). The resulting tablets were coated with a film coating composition consisting of TC-5, polyethylene glycol 6000, castor oil and ethanol into give film-coated tablets of the above composition.

| Pharmaceutical Example 3 | |
|---|---|
| (6S,7S)-7-[2-(2-aminothiazol-4-yl)-2-methoxyiminoacetamide]-3-(1,2,3,4-tetrahydroisoquinolyn-2-yl)methyl-$\Delta^3$-0-2-isocephem-4-carboxylic acid (syn isomer) | 2 g |
| Purified lanolin | 5 g |
| White beeswax | 5 g |
| White petrolatum | 88 g |
| Total | 100 g |

White beeswax was melted by warming and, then, (6S,7S}-7-[2-(2-aminothiazol-4-yl)-2methoxyiminoacetamide]-3-(1,2,3,4-tetrahydroisoquinolyn2-yl)methyl-$\Delta^3$-0-2-isocephem-4-carbonic acid (syn isomer), purified lanolin and white petrolatum were added. The mixture was warmed until it formed a liquid and, then, stirred un&ill it is solidified to give an ointment of the above composition.

| Pharmaceutical Example 4 | |
|---|---|
| (6S,7S)-7-[2-(2-aminothiazol-4-yl)-2-methoxyiminoacetoamido]-3-[(1-pyridinio)methyl]-$\Delta^3$-0-2-isocephem-4-carboxylate (syn isomer) | 200 mg |
| Glucose | 250 mg |
| Distilled water for injection | q.s. |
| Total | 5 ml |

In Distilled water for injection are dissolved (6S,7S)-7-[2-(2-aminoihiazol-4-yl)-2-methoxyiminoacetamido]3-[-(1-pyridinio)methyl]-$\Delta^3$-0-2-isocephem-4-carboxylate (syn isomer) and glucose, and the solution was filled into a 5 ml ampule. After nitrogen purging, sterilization Was carried out by autoclaving at 121° C. for 15 minuted to give a parenteral product of the above composition.

| Phamaceutical Example 5 | |
|---|---|
| (6S,7S)-7-[2-(2-aminothiazol-4-yl)-2-methoxyiminoacetoamide]-3-[(4-cyanomethylthio-1-pyridinio)methyl]-$\Delta^3$-0-2-isocephem-4-carboxylate (syn isomer) | 100 g |
| Avicel (trademark of Asahi Chemical Industry) | 40 g |
| Corn Starch | 30 g |
| Magnesium stearate | 2 g |
| TC-5 (trademark of Shin-Etsu Chemical; hydroxypropylmethyl-cellulose) | 10 g |
| polyethylene glycol 6000 | 3 g |
| Castor oil | 40 g |
| Ethanol | 40 g |

(6S,7S)-7-[2-(2-aminoihiazol-4-yl)-2-methoxyiminoacetamido]-3-[(4-cyanomethylthio-1-pyridinio)-methyl]-$\Delta^3$-0-2-isocephem-4-carboxylate (syn isomer), Avicel, corn starch and magnesium stearate were milled together and tableted by means of R 10 mm punch (for suger-coated tablets). The resulting tablets were coated with a film coating composition consisting of TC-5, polyethylene glycol 6000, castor oil and ethanol to give film-coated tablets of the above composition.

| Pharmaceutical Example 6 | |
|---|---|
| (6S,7S)-7-[2-(2-aminothiazol-4-yl)-2-methoxyiminoacetamide]-3-[[4-(3-pyrazolyl)-1-pyridinio]methyl]-$\Delta^3$-0-2-isocephem-4-carboxylate (syn isomer) | 2 g |
| Purified lanolin | 5 g |
| White beeswax | 5 g |
| White petrolatum | 88 g |

-continued

Pharmaceutical Example 6

Total  100 g

White beeswax was melted by warming and, then, (6S,7)-7-[2-(2-aminothiazol-4-yl)-2-methoxyiminoacetamide]-3-[[4-(8-pyrazolyl)-1pyridinio]methyl]-Δ³-0-2-isocephem-4-carboxylate (syn isomer), purified lanolin and white petrolatum were added. The mixture was warmed until it formed a liquid and, then, stirred until it was solidified to give an ointment of the above composition.

Antimicrobial Activity Test

In order to investigate the in vitro activity of the under-mentioned compounds against various bacteria, the minimal inhibitory concentration (MIC) values were determined by the agar plate dilution method [see Chemotherapy, 22, 1123–1128 (1974)].

The results are shown in Table 1 and Table 2.

Each test inoculum was adjusted to I x 10⁶ cells/ml (O.D., 600m : 0.07–0.16).

Test compounds

No. 1 (6S,7S)-7-[2-(2-aminothiazol-4-yI)-2-methoxyiminoacetamide]-3-(1-pyrolidinyl)methyl-Δ³-0-2-isocephem-4-carboxylic acid (syn isomer)

No. 2 (6S,7S)-7-[2-(2-aminothiazol-4-yl)-2-methoxyiminoacetamide]-3-(I-methyl-1-pyrrolidinio)methyl-Δ³-0-2-isocephem-4-carboxylate (syn isomer)

No. 3 (6S,7S}-7-[2-(2-aminothiazol-4-yl)-2-methoxyiminoacetamide]-3-(1,2,3,4-tetrahydroisoquinolyn-2-yl}methyl-Δ³ -0-2-isocephem-4-carboxylic acid (syn isomer)

No. 4 (6S,7S)-7-[2-(2-aminothiazol-4-Yl)-2-methoxyiminoacetamide]3-(2-methyl-2-1,2,3,4-tetrahydroisoquinoline-2-yl)methyl-Δ³-0-2-isocephem-4-carboxylate (syn isomer)

No. 5 (6S,7S)-7-[2-(2-aminothiazol-4-yl)-2-methoxyiminoacetamide]-3-[(1-pyridinio)methyl]-Δ³-0-2-isocephem-4-carboxylate (syn isomer)

No. 6 (6S,7S)-7-[2-(2-aminothiazol-4-yl}-2-methoxyiminoaoetamide]-3-[(4-cyanomethylthio-1-pyridinio)-methyl]-Δ³-0-2-isocephem-4-carboxylate (syn isomer)

No. 7 (6S,7S}-7-[2-[2-aminothiazol-4-Yl}-2-methoxyiminoacetamide]-3-[[4-(3-pyrazolyl)-1-pyridinio]methyl]-Δ³-0-2-isocephem-4-carboxylate (syn isomer)

No. 8 (6S,7S)-7-[2-(2-aminothiazol-4-yl}-2-isopropyloxyiminoacetamide]-3-[[4-(5-oxazolyl)-1-pyridinio]methyl]-Δ³-0-2-isocephem-4-carboxylate (syn isomer)

No. 9 (6S,7S}-7-[2-(2-aminothiazol-4-yl)-2-cyclopentyloxyiminoacetamide]-3-[[4-(5-oxazolyl)-1-pyridinio]methyl]-Δ³-0-2-isocephem-4carboxylate (syn isomer)

No. 10 (6S,7S)-7-[2-(2-aminothiazol-4-yl)-2- (3-isopropyloxyiminoacetamide]-3-(1-methyl-1pyrrolidinio)-methyl-⁶⁶ ³-0-2-isocephem-4-carboxylate (syn isomer)

No. 11 (6S,7S)-7-[2-(2-aminothiazol-4-yl)-2-cyclopentyloxyiminoacetamide]-3-(I-methyl-1-pyrrolidinio]-methyl-Δ³-0-2-isocephem-4-carboxylate (syn isomer)

No. 12 (6S,7S}-7-[2-(2-amino&hiazol-4-Yl}-2-isopropyloxyiminoacetamide]-3-[(6,7-dihydro-5H-1-pyridinio)]methyl]-Δ³-0-2-isocephem-4-carboxylate (syn isomer)

No. 13 (6S,7S)-7-[2-(2-aminothiazol-4-Yl)-2-allyloxyiminoacetamide]-3-[[4-(5-oxazolyl)-1-pyridinio]methyl]-Δ³-0-2-isocephem-4-carboxylate (syn isomer)

TABLE 1

| Strain | MIC (μg/ml) Test Compound | | | | | | |
|---|---|---|---|---|---|---|---|
| | No. 1 | No. 2 | No. 3 | No. 4 | No. 5 | No. 6 | No. 7 |
| S. aureus FDA-209-p | 1.56 | 0.39 | 0.39 | 0.78 | 0.39 | 0.78 | 0.2 |
| E. coli NIHJ | 0.1 | 0.05 | 0.05 | 0.1 | 0.05 | ≦0.025 | ≦0.025 |
| E. coli No. 29 | 0.1 | 0.05 | 0.05 | 0.05 | 0.05 | ≦0.025 | ≦0.025 |
| K. pneumoniae NCTC-9632 | 0.2 | 0.05 | 0.1 | 0.2 | 0.05 | ≦0.025 | ≦0.025 |
| P. mirabilis ATCC-29906 | 0.2 | 0.1 | 0.1 | 0.2 | 0.1 | ≦0.025 | ≦0.025 |
| M. morganii IIDKono | 0.2 | 0.1 | 0.2 | 0.1 | 0.05 | ≦0.025 | ≦0.025 |
| S. marcescens ATCC-13880 | 0.39 | 0.1 | 0.39 | 0.2 | 0.1 | 0.05 | 0.1 |

TABLE 2

| Strain | MIC (μg/ml) Test Compound | | | | | |
|---|---|---|---|---|---|---|
| | No. 8 | No. 9 | No. 10 | No. 11 | No. 12 | No. 13 |
| S. aureus FDA-209-p | 0.2 | 0.1 | 0.2 | 0.2 | 0.1 | 0.1 |
| E. coli NIHJ | 0.05 | 0.1 | 0.1 | 0.1 | 0.05 | 0.05 |
| E. coli No. 29 | ≦0.05 | 0.05 | 0.1 | 0.1 | ≦0.05 | 0.05 |
| K. pneumoniae NCTC-9632 | ≦0.025 | ≦0.025 | 0.05 | 0.1 | ≦0.025 | ≦0.025 |
| P. mirabilis 1287 | 0.05 | 0.05 | 0.1 | 0.2 | 0.05 | 0.1 |
| M. morganii ATCC-25830 | 0.05 | 0.1 | 0.1 | 0.2 | 0.2 | 0.2 |
| S. marcescens IFO-12648 | 0.2 | 0.2 | 0.39 | 0.39 | 0.39 | 0.2 |
| P. aeruginosa NCTC-10490 | 25 | 12.5 | 12.5 | 12.5 | 25 | 12.5 |

What we claim is:

1. A 2-oxa-isocephem compound of the formula (1):

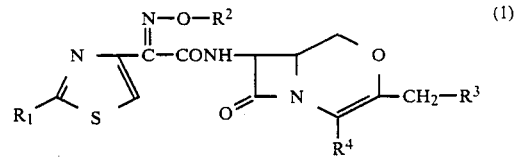

wherein $R^1$ is an amino group which may have a protective group;

$R^2$ is a $C_1$–$C_6$ alkyl group, a $C_3$–$C_8$ cycloalkyl group or a $C_2$–$C_6$ alkenyl group;

$R^3$ is a group of the formula:

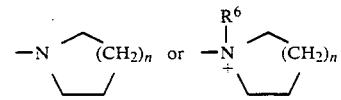

wherein n is 1 or 2, $R^6$ is a $C_1$–$C_6$ alkyl group, these groups may form a condensed ring with a benzene ring; and $R^4$ is a carboxylate group, a carboxy group or an esterified carboxy group; provided that when $R^2$ an is alkyl group, $R^3$ is not a group of the formula:

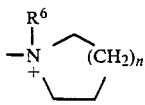

or the pharmaceutically acceptable salt thereof.

2. A 2-oxa-isocephem compound or the pharmaceutically acceptable salt thereof as claimed in claim 1, wherein said amino group represented by $R^1$ and having the protective group is selected from the group consisting of a $C_1$–$C_6$ alkanoylamino group, a $C_2$–$C_6$ alkanoylamino group substituted with 1 to 3 halogen atoms, a phenylalkylamino group substituted with 1 to 3 phenyl groups and having a $C_1$–$C_6$ alkyl moiety, a phenyl alkoxycarbonylamino group having a $C_1$–$C_6$ alkoxy group, and an alkoxycarbonylamino group having a $C_1$–$C_6$ alkoxy moiety.

3. A 2-oxa-ixocephem compound or the pharmaceutically acceptable salt thereof as claimed in claim 1, wherein $R^1$ is an amino group, and $R^4$ is an esterified carboxy group.

4. A 2-oxa-isocephem compound or the pharmaceutically acceptable salt thereof as claimed in claim 1, wherein $R^1$ is an amino group, and $R^4$ is a carboxy group or a carboxylate group.

5. A 2-oxa-isocephem compound or the pharmaceutically acceptable salt thereof as claimed in claim 4, wherein $R^3$ is represented by the formula:

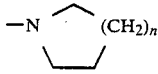

wherein n is 1 or 2.

6. A 2-oxa-isocephem compound or the pharmaceutically acceptable salt thereof as claimed in claim 5, wherein $R^2$ is a $C_1$–$C_6$ alkyl group or a $C_3$–$C_6$ cycloalkyl group.

7. A 2-oxa-ixocephem compound or the pharmaceutically acceptable salt thereof as claimed in claim 4, wherein $R^3$ is represented by the formula:

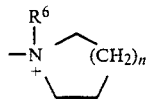

wherein n is 1 or 2, and $R^6$ is a $C_1$–$C_6$ alkyl group.

8. A 2-oxa-isocephem compound or the pharmaceutically acceptable salt thereof as claimed in claim 7, wherein $R^2$ is a $C_3$–$C_8$ cycloalkyl group.

9. A 2-oxa-isocephem compound or the pharmaceutically acceptable salt thereof as claimed in claim 7, wherein $R^2$ is a $C_2$–$C_6$ alkenyl group.

10. A 2-oxa-isocephem compound or the pharmaceutically acceptable salt thereof as claimed in claim 8, wherein $R^3$ does not form a condensed ring with a benzene ring.

11. A 2-oxa-isocephem compound or the pharmaceutically acceptable salt thereof as claimed in claim 8, wherein $R^3$ forms a condensed ring with a benzene ring.

12. A 2-oxa-isocephem compound or the pharmaceutically acceptable salt thereof as claimed in claim 10, wherein said compound is (6S, 7S)-7-(2-(2-aminothiazole-4-yl)-2-cyclopentyloxyiminoacetamido)-3-(1-methyl-1-pyrrolidinio)methyl-$\Delta^3$-0-2-isocephem-4-carboxylate (syn isomer).

13. A 2-oxa-isocephem compound or the pharmaceutically acceptable salt thereof as claimed in claim 9, wherein $R^3$ does not form a condensed ring with a benzene ring.

14. An antimicrobial composition comprising
 (i) an antimicrobially effective amount of a 2-oxa-isocephem compound of the formula (1) as defined in claim 1 or a pharmaceutically acceptable salt thereof, and
 (ii) a pharmaceutically acceptable carrier.

* * * * *

UNITED STATES PATENT AND TRADEMARK OFFICE
CERTIFICATE OF CORRECTION

PATENT NO. : 4,950,662

DATED : August 21, 1990

INVENTOR(S) : Setsuro Fujii, Hiroshi Ishikawa, Koichi Yasumura, Koichiro Jitsukawa, Sachio Toyama, Hidetsugu Tsubouchi, Kimio Sudo and Koichi Tsuji It is certified that error appears in the above-identified patent and that said Letters Patent is hereby corrected as shown below:

Title page of issued patent, Section [30] "Foreign Application Priority Data", include the following information:

-- Sept. 27, 1988 [JP] Japan ................. 63-243387 --.

Signed and Sealed this

Twenty-eighth Day of July, 1992

Attest:

DOUGLAS B. COMER

Attesting Officer

Acting Commissioner of Patents and Trademarks